(12) United States Patent
Nishio et al.

(10) Patent No.: US 11,865,232 B2
(45) Date of Patent: Jan. 9, 2024

(54) SCATTERING DEVICE AND DOOR

(71) Applicant: PANASONIC INTELLECTUAL PROPERTY CORPORATION OF AMERICA, Torrance, CA (US)

(72) Inventors: Yuri Nishio, Tokyo (JP); Yosuke Akita, Osaka (JP); Masazumi Watanabe, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 876 days.

(21) Appl. No.: 16/903,648

(22) Filed: Jun. 17, 2020

(65) Prior Publication Data

US 2020/0397939 A1 Dec. 24, 2020

(30) Foreign Application Priority Data

Jun. 18, 2019 (JP) .................................. 2019-112951

(51) Int. Cl.
| | |
|---|---|
| *A61L 9/14* | (2006.01) |
| *B05B 12/12* | (2006.01) |
| *B05B 7/24* | (2006.01) |
| *A61L 9/12* | (2006.01) |
| *E06B 5/00* | (2006.01) |
| *E06B 7/28* | (2006.01) |
| *G01L 5/00* | (2006.01) |
| *G01P 15/00* | (2006.01) |
| *G06V 40/20* | (2022.01) |
| *G06V 40/16* | (2022.01) |

(52) U.S. Cl.
CPC .................. *A61L 9/14* (2013.01); *A61L 9/12* (2013.01); *B05B 7/2491* (2013.01); *B05B 12/122* (2013.01); *E06B 5/00* (2013.01); *E06B 7/28* (2013.01); *G01L 5/00* (2013.01); *G01P 15/00* (2013.01); *A61L 2209/111* (2013.01); *A61L 2209/134* (2013.01); *G06V 40/161* (2022.01); *G06V 40/172* (2022.01); *G06V 40/20* (2022.01)

(58) Field of Classification Search
CPC ... A61L 9/015; A61L 9/02; A61L 9/03; A61L 9/032; A61L 9/035; A61L 9/04; A61L 9/12; A61L 9/122; A61L 9/125; A61L 9/14; E05B 5/00; E06B 7/28; B05B 12/122
See application file for complete search history.

(56) References Cited

U.S. PATENT DOCUMENTS

2018/0225551 A1* 8/2018 Lin .................. A61L 9/122

FOREIGN PATENT DOCUMENTS

| JP | 2015-136698 | | 7/2015 | |
|---|---|---|---|---|
| WO | WO-2018022562 A1 | * | 2/2018 | ............ A01M 29/12 |

* cited by examiner

*Primary Examiner* — Timothy C Cleveland
(74) *Attorney, Agent, or Firm* — Greenblum & Bernstein, P.L.C.

(57) ABSTRACT

A scattering device includes a position detection unit which detects a position of a user passing through a doorway formed between a first space and a second space adjacent to the first space; a scattering direction determination unit which determines a scattering direction in which liquid, powder, or gas is scattered from proximity of the doorway based on the position of the user detected by the position detection unit; and a scattering unit arranged in the proximity of the doorway to scatter the liquid, the powder, or the gas toward the scattering direction determined by the scattering direction determination unit.

10 Claims, 19 Drawing Sheets

SCATTERING DEVICE AND DOOR

FIELD OF THE INVENTION

The present disclosure relates to a technique for scattering liquid, powder, or gas.

BACKGROUND ART

There have been conventionally provided an automatic scattering device in a storage, the device automatically scattering a spray liquid such as a disinfectant liquid, a sterilizing liquid, a bactericidal liquid, an aromatic liquid, and a deodorizing liquid into the storage whenever a door of the storage is opened/closed (see e.g. Japanese Unexamined Patent Publication No. 2015-136698).

For example, the automatic scattering device in a storage as disclosed in Japanese Unexamined Patent Publication No. 2015-136698 includes a press-in operation mechanism for pressing a push button and releasing the press-in by the opening/closing action of an opening/closing tool. The press-in operation mechanism includes a cam-operated arm having a tip end portion to be in contact with and separated from the opening/closing tool and having a taper cam formed on a body portion, the taper cam slidably contacting with a head of the push button to press in the push button and release the pressing-in; a spring mechanism for energizing the cam-operated arm so as to enable reciprocating sliding; and a frame body formed with a scattering opening portion so as to be detachably attached to an upper part of a spray liquid storing portion.

However, with the above conventional technique, a spray liquid can be scattered into only one of two adjacent spaces and is therefore demanded to be further improved.

SUMMARY OF THE INVENTION

The present disclosure has been made to solve the above problem, and an object thereof is to provide a technique for scattering liquid, powder, or gas in a direction in which a user heads.

A scattering device according to one aspect of the present disclosure is a scattering device which scatters liquid, powder, or gas, the scattering device including a detection unit which detects a position of a user passing through a doorway formed between a first space and a second space adjacent to the first space; a scattering direction determination unit which determines a scattering direction in which the liquid, the powder, or the gas is scattered from proximity of the doorway based on the position of the user detected by the detection unit; and a scattering unit arranged in the proximity of the doorway to scatter the liquid, the powder, or the gas toward the scattering direction determined by the scattering direction determination unit.

DESCRIPTION OF EMBODIMENTS

Knowledge Underlying the Present Disclosure

Figure 1:
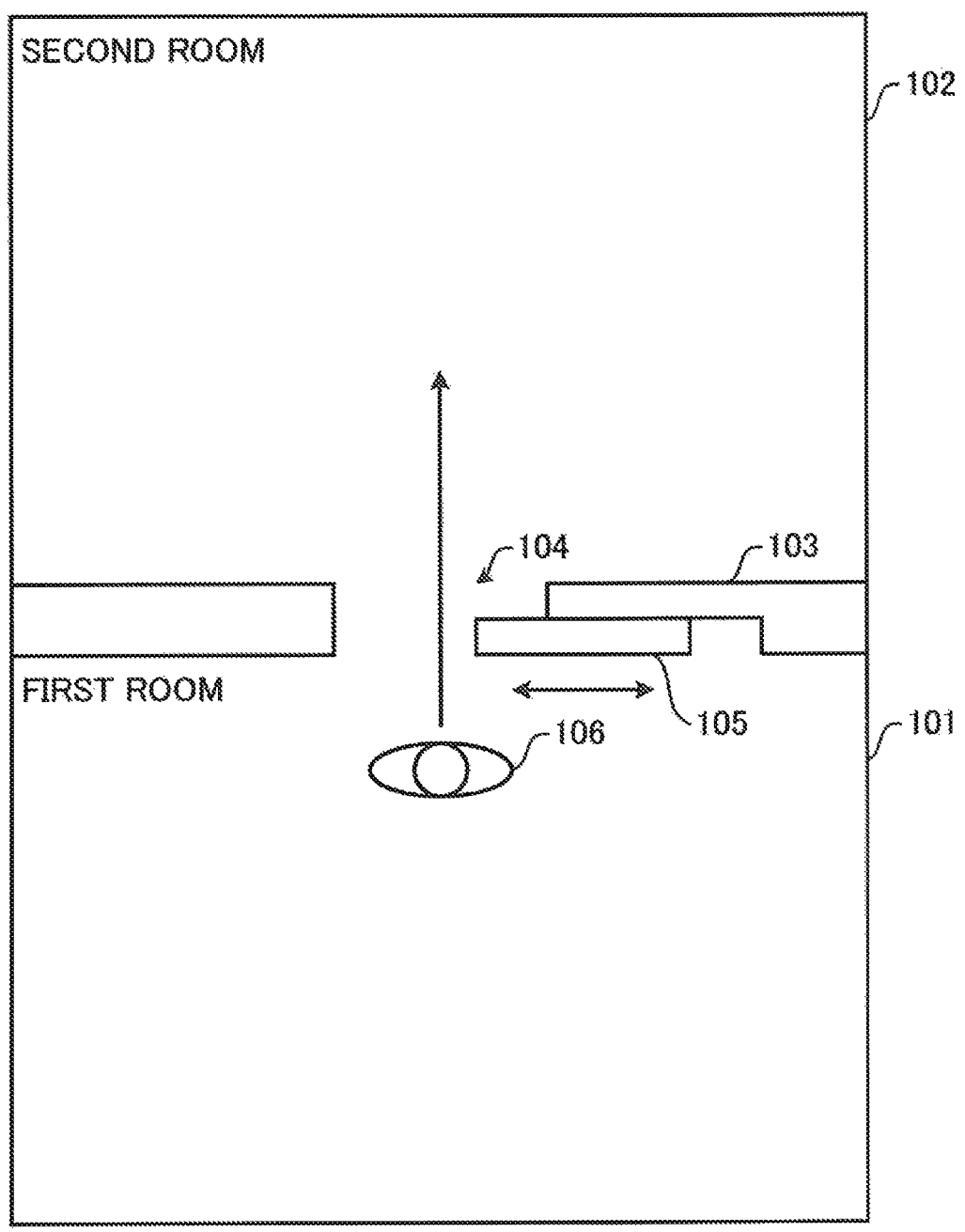
FIG. 1 is a schematic view for describing user's movement in a first embodiment of the present disclosure.

In recent years, people have been making positive use of scent in a living space by, for example, placing an air freshener in a house. For example, it is possible to provide a user with a comfortable space by scattering scent at a timing when a user opens a door.

For example, although in a conventional device, a spray liquid is scattered in association with opening/closing operation of a door, the spray liquid can be scattered only in one of two spaces partitioned by the door, and it is therefore difficult to scatter a spray liquid based on a user's position.

In order to solve the above problem, a scattering device according to one aspect of the present disclosure is a scattering device which scatters liquid, powder, or gas, the scattering device including: a detection unit which detects a position of a user passing through a doorway formed between a first space and a second space adjacent to the first space; a scattering direction determination unit which determines a scattering direction in which the liquid, the powder, or the gas is scattered from proximity of the doorway based on the position of the user detected by the detection unit; and a scattering unit arranged in the proximity of the doorway to scatter the liquid, the powder, or the gas toward the scattering direction determined by the scattering direction determination unit.

According to this configuration, since a scattering direction in which the liquid, the powder, or the gas is scattered from the proximity of the doorway is determined based on a position of a user passing through the doorway formed between the first space and the second space adjacent to the first space, liquid, powder, or gas can be scattered in a direction in which a user heads.

In the above scattering device, the scattering direction determination unit may determine a direction in which the user moves from the proximity of the doorway as the scattering direction.

According to this configuration, since a direction in which a user moves from the proximity of the doorway is determined as a scattering direction, liquid, powder, or gas can be scattered in a direction in which the user moves from the proximity of the doorway.

In the above scattering device, the liquid, the powder, or the gas may include an aromatic substance.

According to this configuration, for example, when a user moves from the first space to the second space, an aromatic substance can be scattered in a direction in which a user heads, and a comfortable space can be provided for the user.

In the above scattering device, the aromatic substance to be scattered when the user moves from the first space to the second space and the aromatic substance to be scattered when the user moves from the second space to the first space may be different from each other.

According to this configuration, since the aromatic substance to be scattered when the user moves from the first space to the second space and the aromatic substance to be scattered when the user moves from the second space to the first space are different from each other, user's movement can be recognized by scent.

In the above scattering device, the doorway may include a door, and the scattering unit may include a first scattering opening provided in proximity to the door on a first space side to scatter the liquid, the powder, or the gas; a second scattering opening provided in proximity to the door on a second space side to scatter the liquid, the powder, or the gas; a duct connected to the first scattering opening and the second scattering opening; a pump which sends air to the duct by using power of the user for opening the door; a storage unit provided in the duct to store the liquid, the powder, or the gas and send out the liquid, the powder, or the gas as a result of passing of the air sent from the pump; and a switching unit which switches a sending destination of the liquid, the powder, or the gas sent out from the storage unit to one of the first scattering opening and the second scattering opening.

According to this configuration, liquid, powder, or gas can be scattered from one of the first scattering opening and the second scattering opening at a user's movement destination by opening of the door by the user.

The above scattering device may further include a time obtaining unit which obtains current time; and a kind determining unit which determines a kind of the liquid, the powder, or the gas according to the current time obtained by the time obtaining unit.

According to this configuration, for example, by changing a kind of liquid, powder, or gas in a morning time zone and an afternoon time zone, a user can recognize time change by a change of liquid, powder, or gas to be scattered.

In the above scattering device, the doorway may include a door, and the scattering device may further include a load measuring unit which measures a load applied on the door when the user opens the door; a user information storage unit which stores user information that correlates identification information for identifying the user, age of the user, gender of the user, and a kind of the liquid, the powder, or the gas; an estimation unit which estimates age and gender corresponding to the load measured by the load measuring unit; and a kind specifying unit which refers to the user information stored in the user information storage unit to specify a kind of the liquid, the powder, or the gas correlated with the age and the gender estimated by the estimation unit.

According to this configuration, age and gender of a user are estimated from a load applied on a door when the user opens the door, and a kind of liquid, powder, or gas desired by the user can be specified from the estimated age and gender. Accordingly, by opening of the door by the user, it is possible to scatter liquid, powder, or gas of a kind desired by the user who opened the door.

In the above scattering device, the doorway may include a door, and the scattering device may further include a load measuring unit which measures a load applied on the door when the user opens the door; an acceleration measuring unit which measures an acceleration of the door when the user opens the door; a prediction unit which inputs, to a prediction model obtained by machine learning using teaching data with the load and the acceleration as input data and emotion of the user as output data, the load measured by the load measuring unit and the acceleration measured by the acceleration measuring unit, and predicts, as emotion of the user when the user opens the door, emotion output from the prediction model; and a kind determining unit which determines a kind of the liquid, the powder, or the gas according to the emotion predicted by the prediction unit.

According to this configuration, since the emotion of the user when the user opens the door is predicted from a load applied on the door when the user opens the door and an acceleration of the door when the user opens the door, and a kind of liquid, powder, or gas is determined according to the predicted emotion. Accordingly, by opening of the door by the user, it is possible to scatter liquid, powder, or gas of a kind according to emotion of the user who opened the door.

In the above scattering device, when the user moves from the first space to the second space, the scattering direction determination unit determines, as the scattering direction, a direction from the proximity of the doorway toward the second space, and the scattering device may further include an odor sensor which measures an odor concentration in the first space; and a scatter amount determination unit which determines a scatter amount of the liquid, the powder, or the gas according to the odor concentration of the first space measured by the odor sensor when the user moves from the first space to the second space.

According to this configuration, when the user moves from the first space to the second space, an odor concentration in the first space is measured, and according to the measured odor concentration of the first space, the scatter amount of the liquid, the powder, or the gas is determined. It is accordingly possible to allow a user to more reliably recognize odor by, for example, when the odor concentration in the first room is high, increasing the amount of liquid, powder, or gas to be scattered in the second room.

A door according to another aspect of the present disclosure includes the scattering device according to any of the above configurations. According to this configuration, the above scattering device is applicable to a door.

With reference to the accompanying drawings, embodiments of the present disclosure will be described in the following. Each of the embodiments shown below is one example of implementation of the present disclosure and do not limit a technical range of the present disclosure.

First Embodiment

FIG. 1 is a schematic view for describing user's movement in a first embodiment of the present disclosure. FIG. 1 is a view of a house of a user 106 seen from above.

In FIG. 1, a wall 103 is provided on the border between a first room 101 and a second room 102 adjacent to the first room 101. The wall 103 is formed with a doorway 104. The user 106 passes through the doorway 104 formed between the first room 101 and the second room 102. The first room 101 is one example of the first space and the second room 102 is one example of the second space.

The doorway 104 includes a door 105. The user 106 in the first room 101 opens the door 105 from the first room 101 side to move into the second room 102. The user 106 in the second room 102 opens the door 105 from the second room 102 side to move into the first room 101. Although the door 105 in the first embodiment is of a sliding door type, the present disclosure is not particularly limited thereto and the door may be of a hinged door type. The doorway 104 may not include the door 105.

Figure 2:
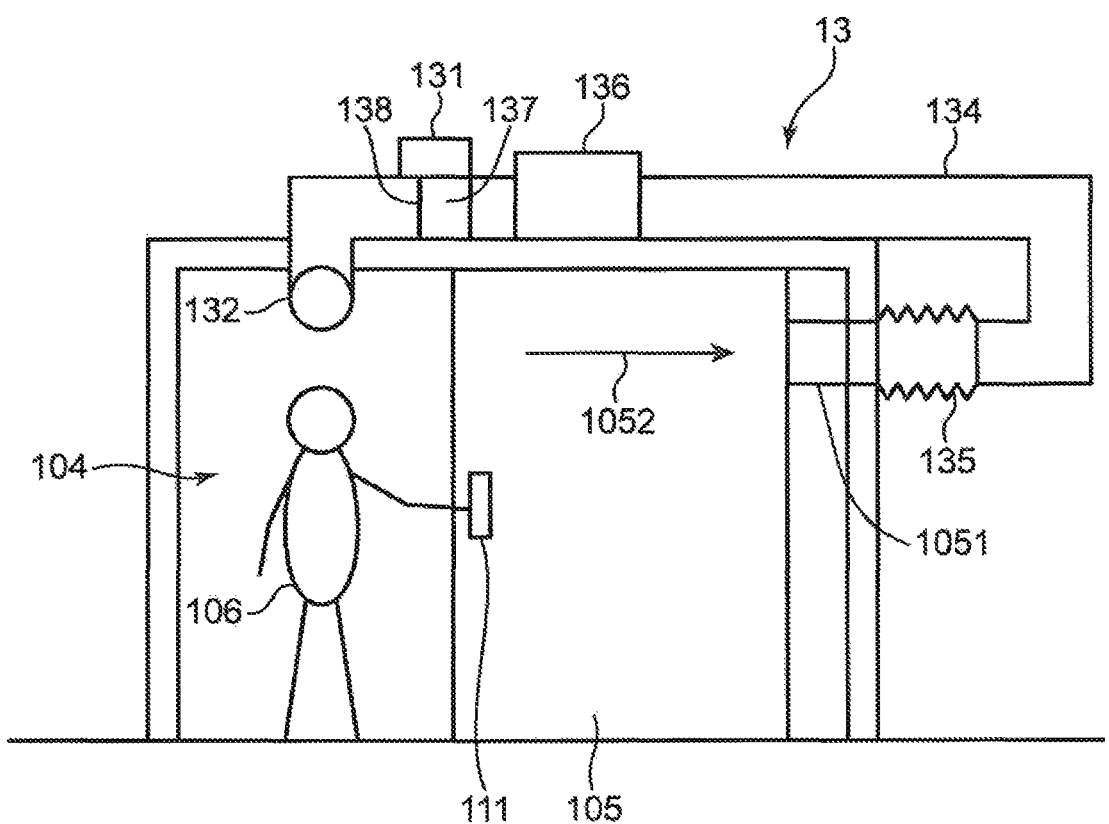
FIG. 2 is a view of a doorway seen from a first room side in the first embodiment of the present disclosure.
Figure 3:
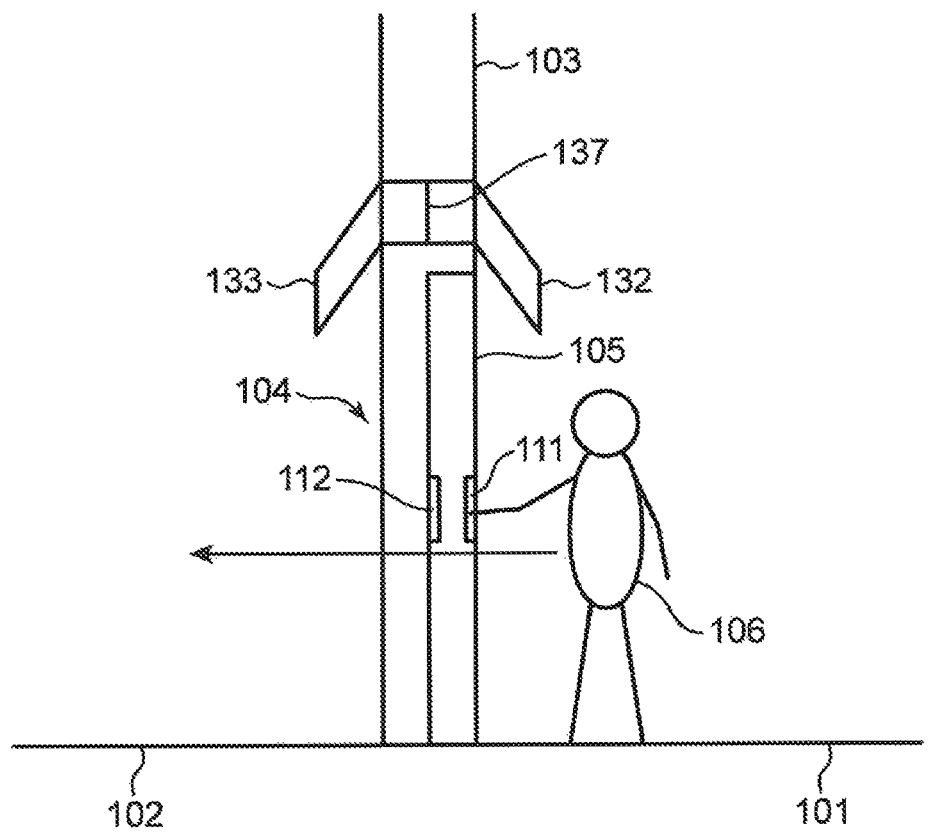
FIG. 3 is a view of the doorway seen from the side in the first embodiment of the present disclosure.
Figure 4:
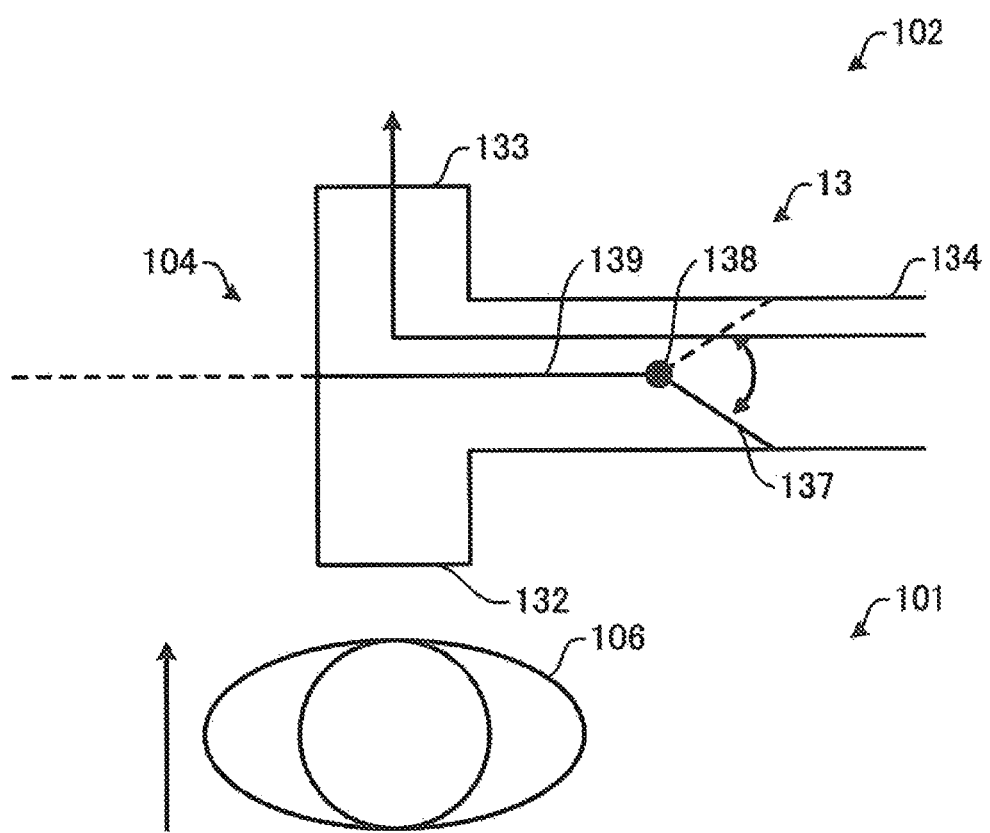
FIG. 4 is a sectional view of a duct of a scattering unit seen from above in the first embodiment of the present disclosure.
Figure 5:
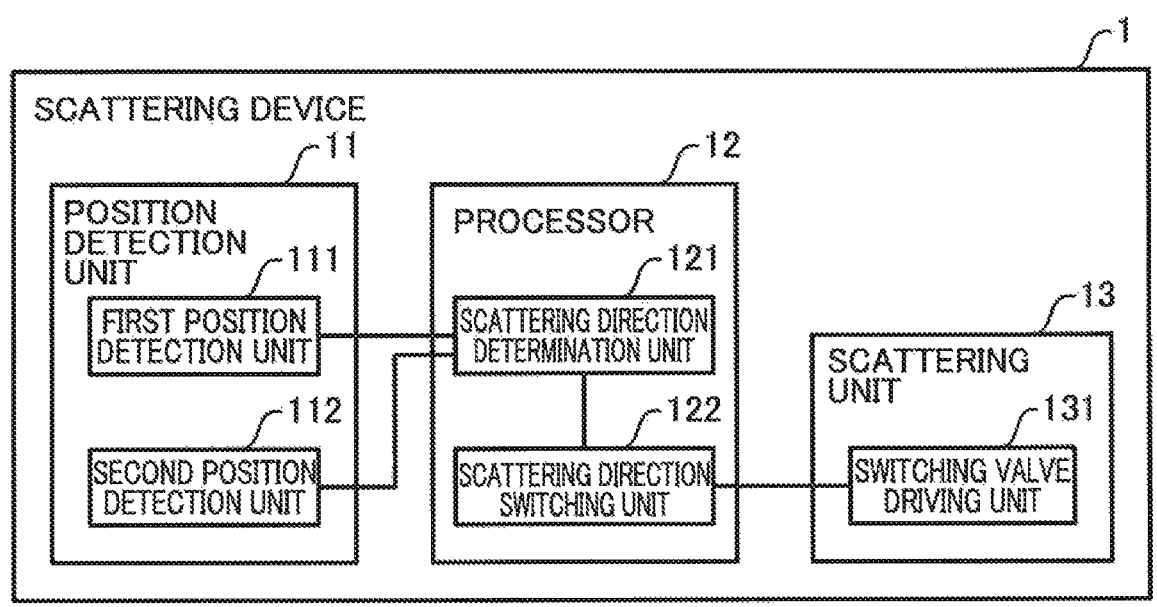
FIG. 5 is a block diagram showing a configuration of a scattering device in the first embodiment of the present disclosure.

FIG. 2 is a view of the doorway seen from the first room side in the first embodiment of the present disclosure, FIG. 3 is a view of the doorway seen from the side in the first embodiment of the present disclosure, FIG. 4 is a sectional view of a duct of a scattering unit seen from above in the first embodiment of the present disclosure, and FIG. 5 is a block diagram showing a configuration of a scattering device in the first embodiment of the present disclosure.

A scattering device 1 includes a position detection unit 11, a processor 12, and a scattering unit 13.

The position detection unit 11 detects a position of the user 106 passing through the doorway 104 formed between the first room 101 and the second room 102 adjacent to the first room 101. The position detection unit 11 includes a first position detection unit 111 and a second position detection unit 112.

The first position detection unit 111, which is configured by, for example, a capacitance type touch sensor, is arranged at a handle portion of the door 105 on the first room 101 side. The first position detection unit 111 detects whether or not the handle portion is touched by the user 106. When the user 106 opens the door 105 from the first room 101 side, the user 106 touches the handle portion of the door 105 on the first room 101 side. At this time, the first position detection unit 111 detects the user 106 touching the door and outputs a detection signal.

The second position detection unit 112 is configured by, for example, a capacitance type touch sensor, and is arranged at a handle portion of the door 105 on the second room 102 side. The second position detection unit 112 detects whether or not the handle portion is touched by the user 106. When the user 106 opens the door 105 from the second room 102 side, the user 106 touches the handle portion of the door 105 on the second room 102 side. At this time, the second position detection unit 112 detects the user 106 touching the door and outputs the detection signal.

The processor 12, which is configured by, for example, a central processing unit (CPU), includes a scattering direction determination unit 121 and a scattering direction switching unit 122.

The scattering direction determination unit 121 determines a scattering direction in which liquid, powder, or gas is scattered from the proximity of the doorway 104 based on a position of the user 106 detected by the position detection unit 11. The scattering direction determination unit 121 determines, as a scattering direction, a direction in which the user 106 moves from the proximity of the doorway 104. When touch by the user 106 is detected by the first position detection unit 111, a direction of movement of the user 106 is a direction from the first room 101 toward the second room 102. Then, when the touch by the user 106 is detected by the first position detection unit 111, the scattering direction determination unit 121 determines a direction from the proximity of the doorway 104 toward the second room 102 as a second scattering direction. When touch by the user 106 is detected by the second position detection unit 112, a direction of movement of the user 106 is a direction from the second room 102 toward the first room 101. Therefore, when the touch by the user 106 is detected by the second position detection unit 112, the scattering direction determination unit 121 determines a direction from the proximity of the doorway 104 toward the first room 101 as a first scattering direction.

The scattering direction switching unit 122 switches a scattering direction in which liquid, powder, or gas is scattered to a scattering direction determined by the scattering direction determination unit 121. The scattering direction switching unit 122 outputs, to a switching valve driving unit 131, a scattering direction switching signal for switching a scattering direction in which liquid, powder, or gas is scattered between the first scattering direction from the proximity of the doorway 104 toward the first room 101 and the second scattering direction from the proximity of the doorway 104 toward the second room 102.

The scattering unit 13, which is arranged in the proximity of the doorway 104, scatters liquid, powder, or gas toward a scattering direction determined by the scattering direction determination unit 121.

The scattering unit 13 includes the switching valve driving unit 131, a first scattering opening 132, a second scattering opening 133, a duct 134, a pump 135, a storage unit 136, and a switching valve 137.

The first scattering opening 132, which is provided in proximity to the door 105 on the first room 101 side, scatters liquid, powder, or gas. The first scattering opening 132 is provided above the door 105 on the first room 101 side. The first scattering opening 132 scatters liquid, powder, or gas toward the user 106 who has moved from the second room 102 to the first room 101.

The second scattering opening 133, which is provided in proximity to the door 105 on the second room 102 side, scatters liquid, powder, or gas. The second scattering opening 133 is provided above the door 105 on the second room 102 side. The second scattering opening 133 scatters liquid, powder, or gas toward the user 106 who has moved from the first room 101 to the second room 102.

The duct 134 is connected to the first scattering opening 132 and the second scattering opening 133. The duct 134 is provided above the door 105.

The pump 135 sends air to the duct 134 by using power of the user 106 for opening the door 105. The pump 135 is pleated and extends and contracts in a direction 1052 in which the door 105 opens. As shown in FIG. 2, of two faces of the door 105 which are vertical to the direction 1052 in which the door 105 opens, on a face opposite to the handle, a protrusion 1051 for pressing in the pump 135 is formed. Opening of the door 105 causes the protrusion 1051 to press in the pump 135 and causes the pump 135 to contract. Contraction of the pump 135 causes air in the pump 135 to be sent out to the duct 134.

The storage unit 136, which is provided in the duct 134, stores liquid, powder, or gas to be scattered. The storage unit 136 sends out liquid, powder, or gas as a result of passing of air sent from the pump 135. The storage unit 136 stores, e.g., a liquid scattering substance. When air enters the storage unit 136, the vaporized scattering substance is sent out from the storage unit 136.

The switching valve 137 switches a sending destination of liquid, powder, or gas sent from the storage unit 136 to one of the first scattering opening 132 and the second scattering opening 133. The switching valve 137 has, for example, a square shape. As shown in FIG. 4, a rotation shaft 138 extending in a vertical direction is provided between the first scattering opening 132 and the second scattering opening 133 and the storage unit 136. To the rotation shaft 138, a partition plate 139 is connected which partitions a space in the duct 134 into a space on the first scattering opening 132 side and a space on the second scattering opening 133 side. Also, one side of the switching valve 137 is attached to the rotation shaft 138. As a result of rotation of the rotation shaft 138, the other side opposed to the one side of the switching valve 137 contacts with either a side face of the duct 134 on the first scattering opening 132 side or a side face of the duct 134 on the second scattering opening 133 side.

Contact of the other side of the switching valve 137 with the side face of the duct 134 on the first scattering opening 132 side forms a path on which liquid, powder, or gas heads toward the second scattering opening 133. Contact of the other side of the switching valve 137 with the side face of the duct 134 on the second scattering opening 133 side forms a path on which liquid, powder, or gas heads toward the first scattering opening 132.

The switching valve driving unit 131 causes the rotation shaft 138 to which the switching valve 137 is attached to rotate based on the scattering direction switching signal output from the scattering direction switching unit 122. When switching to the first scattering direction from the proximity of the doorway 104 toward the first room 101, the switching valve driving unit 131 causes the rotation shaft 138 to rotate such that the switching valve 137 moves to the second scattering opening 133 side. As a result, a path from the duct 134 toward the second scattering opening 133 is blocked to form a path from the duct 134 toward the first scattering opening 132. When switching to the second scattering direction from the proximity of the doorway 104 toward the second room 102, the switching valve driving unit 131 causes the rotation shaft 138 to rotate such that the switching valve 137 moves to the first scattering opening 132 side. As a result, the path from the duct 134 toward the first scattering opening 132 is blocked to form a path from the duct 134 toward the second scattering opening 133.

In the first embodiment, liquid, powder, or gas to be scattered is an aromatic substance. The aromatic substance is scattered from the first scattering opening 132 or the second scattering opening 133. For example, by scattering an aromatic substance having a relaxing effect, a comfortable space can be provided at a timing when the user 106 moves from one space to another space.

Also in the first embodiment, liquid, powder, or gas to be scattered is not limited to an aromatic substance but may be a disinfectant substance, a sterilizing substance, a bactericidal substance, or a deodorizing substance.

The scattering unit 13 may include a check valve provided between the duct 134 and the pump 135. The check valve is a value for preventing backflow of air from the duct 134 side to the pump 135 after the pump 135 sends out air to the duct 134. The pump 135 does not take in air from the duct 134 after sending out air to the duct 134, but takes in air through an air hole separately provided between the duct 134 and the pump 135 and extends and contracts.

Subsequently, operation of the scattering device 1 in the first embodiment will be described.

Figure 6:
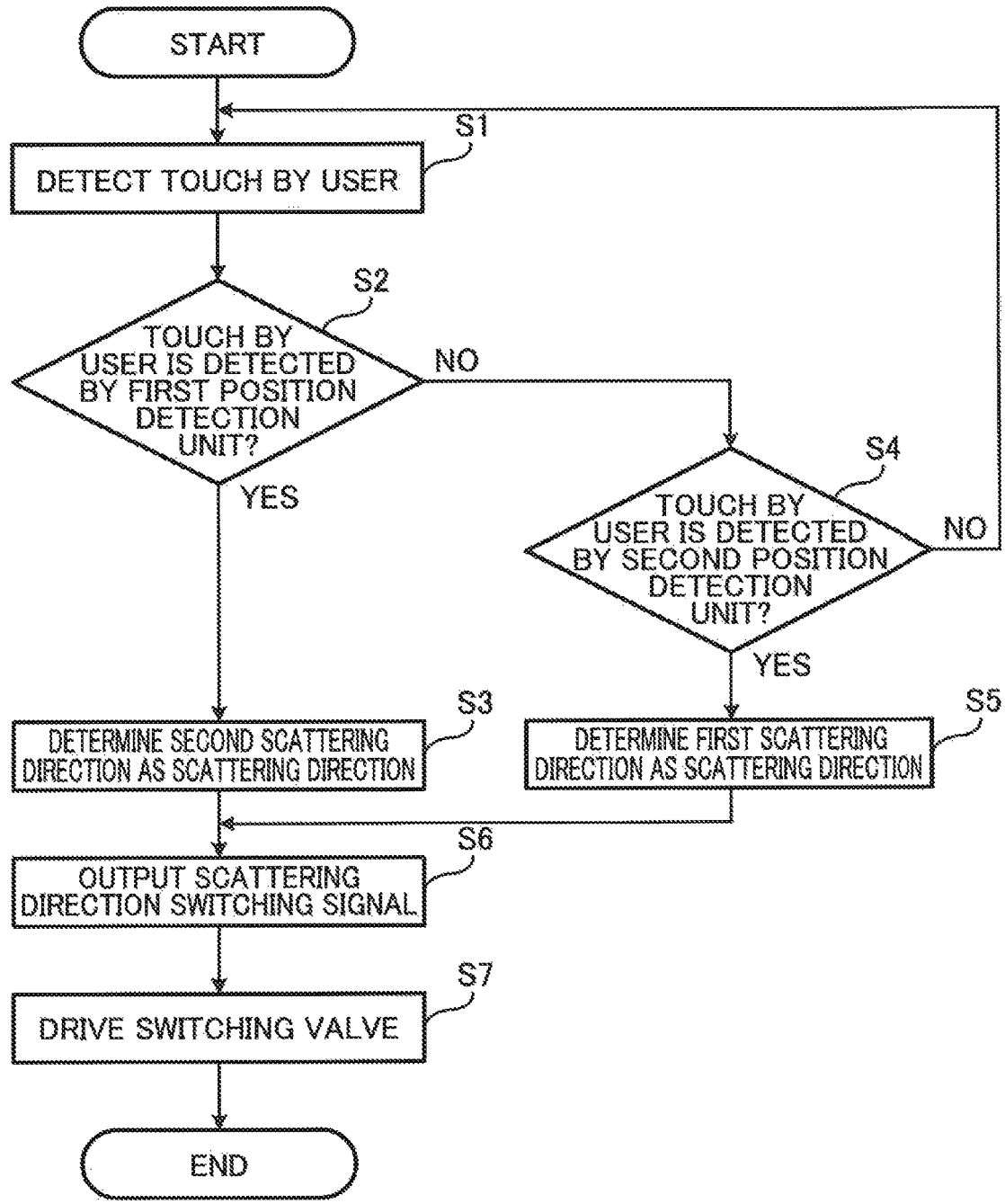
FIG. 6 is a flow chart for describing operation of the scattering device in the first embodiment of the present disclosure.

FIG. 6 is a flow chart for describing operation of the scattering device in the first embodiment of the present disclosure.

First, in Step S1, the first position detection unit 111 and the second position detection unit 112 detect touch by the user 106. When touch by the user 106 is detected, the first position detection unit 111 outputs the detection signal to the scattering direction determination unit 121. When touch by the user 106 is detected, the second position detection unit 112 outputs the detection signal to the scattering direction determination unit 121.

Next, in Step S2, the scattering direction determination unit 121 determines whether or not touch by the user 106 is detected by the first position detection unit 111.

Here, when determination is made that the first position detection unit 111 detects touch by the user 106 (YES in Step S2), the scattering direction determination unit 121 determines the second scattering direction from the proximity of the doorway 104 toward the second room 102 as a scattering direction in Step S3.

By contrast, when determination is made that touch by the user 106 is not detected by the first position detection unit 111 (NO in Step S2), the scattering direction determination unit 121 determines whether or not touch by the user 106 is detected by the second position detection unit 112 in Step S4.

Here, when determination is made that touch by the user 106 is not detected by the second position detection unit 112 (NO in Step S4), the processing returns to Step S1.

By contrast, when determination is made that touch by the user 106 is detected by the second position detection unit 112 (YES in Step S4), the scattering direction determination unit 121 determines the first scattering direction from the proximity of the doorway 104 toward the first room 101 as a scattering direction in Step S5.

Next, in Step S6, the scattering direction switching unit 122 outputs, to the switching valve driving unit 131, the scattering direction switching signal which switches a scattering direction in which liquid, powder, or gas is scattered to one of the first scattering direction from the proximity of the doorway 104 toward the first room 101 and the second scattering direction from the proximity of the doorway 104 toward the second room 102.

Next, in Step S7, by causing the rotation shaft 138 to which the switching valve 137 is attached to rotate, the switching valve driving unit 131 drives the switching valve 137 based on the scattering direction switching signal output from the scattering direction switching unit 122. Then, upon opening of the door 105 by the user 106, gas will be scattered to an advancing direction of the user 106.

Since a scattering direction in which liquid, powder, or gas is scattered from the proximity of the doorway 104 is determined based on a position of the user 106 passing through the doorway 104 formed between the first room 101 and the second room 102 adjacent to the first room 101 in this manner, liquid, powder, or gas can be scattered in the direction in which the user 106 heads.

Although in the first embodiment, the first position detection unit 111 and the second position detection unit 112, which are, for example, touch sensors arranged at the handle portion of the door 105, detect whether or not the user 106 touches, the present disclosure is not particularly limited thereto. The first position detection unit 111 and the second position detection unit 112 may be, for example, a human sensor which detects a person in front of the door 105. In this case, the first position detection unit 111 detects whether or not a user is present in front of the door 105 on the first room 101 side. The second position detection unit 112 detects whether or not a user is present in front of the door 105 on the second room 102 side. In a case where the first position detection unit 111 detects that a user is present in front of the door 105 on the first room 101 side, the scattering direction determination unit 121 may determine, as a scattering direction, the direction from the proximity of the doorway 104 toward the second room 102. In a case where the second position detection unit 112 detects that a user is present in front of the door 105 on the second room 102 side, the scattering direction determination unit 121 may determine, as a scattering direction, the direction from the proximity of the doorway 104 toward the first room 101.

Although the door 105 in the first embodiment is of a sliding door type, the present disclosure is not particularly limited thereto and the door may be of a hinged door type. In this case, the first position detection unit 111 and the second position detection unit 112 are, for example, touch sensors arranged at a doorknob of the door 105, and may detect whether or not the doorknob is touched by the user 106. Also, the first position detection unit 111 may detect a doorknob on the first room 101 side being turned and the second position detection unit 112 may detect a doorknob on the second room 102 side being turned.

Further, in a case where the door 105 is of a hinged door type, the position detection unit 11 may measure a load applied on a hinge for attaching the door 105 to the wall 103. In this case, the position detection unit 11 may measure a load applied on the hinge on the first room 101 side and a load applied on the hinge on the second room 102 side. Then, in a case where the load applied on the hinge on the first room 101 side is larger than the load applied on the hinge on the second room 102 side, the position detection unit 11 determines that the user 106 is present in front of the door 105 on the first room 101 side. In a case where the load applied on the hinge on the first room 101 side is smaller than the load applied on the hinge on the second room 102 side, the position detection unit 11 also determines that the user 106 is present in front of the door 105 on the second room 102 side.

Further, in a case where the door 105 is of a sliding door type, the position detection unit 11 may measure a load applied on a roller provided on an upper portion of the door 105 or a guide pin provided on a lower portion of the door 105. In this case, the position detection unit 11 may measure a load applied on the roller or the guide pin on the first room 101 side and a load applied on the roller or the guide pin on the second room 102 side. Then, in a case where the load applied on the roller or the guide pin on the first room 101 side is larger than the load applied on the roller or the guide pin on the second room 102 side, the position detection unit 11 determines that the user 106 is present in front of the door 105 on the first room 101 side. Also, in a case where the load applied on the roller or the guide pin on the first room 101 side is smaller than the load applied on the roller or the guide pin on the second room 102 side, the position detection unit 11 determines that the user 106 is present in front of the door 105 on the second room 102 side.

Although in the first embodiment, an aromatic substance to be scattered when the user moves from the first room 101 to the second room 102 and an aromatic substance to be scattered when the user moves from the second room 102 to the first room 101 are the same, the present disclosure is not particularly limited thereto, and the aromatic substances may be changed based on a line of movement of the user 106. Specifically, the aromatic substance to be scattered when the user moves from the first room 101 to the second room 102 and the aromatic substance to be scattered when the user moves from the second room 102 to the first room 101 can be different from each other. In this case, the scattering unit 13 may not include the storage unit 136 arranged between the pump 135 and the switching valve 137, but may include a first storage unit arranged between the switching valve 137 and the first scattering opening 132 and a second storage unit arranged between the switching valve 137 and the second scattering opening 133. The first storage unit stores liquid, powder, or gas including a first kind of aromatic substance. The second storage unit stores liquid, powder, or gas including a second kind, which is different from the first kind, of aromatic substance.

Also, while in the first embodiment, the pump 135 sends air to the duct 134 by using power of the user 106 for opening the door 105, the present disclosure is not particularly limited thereto, and the scattering unit 13 may include a first spray unit arranged above the door 105 on the first room 101 side for automatically spraying an aromatic substance by electric power and a second spray unit arranged above the door 105 on the second room 102 side for automatically spraying an aromatic substance by electric power. In a case where the first scattering direction from the proximity of the doorway 104 toward the first room 101 is determined as a scattering direction, the scattering direction switching unit 122 transmits, to the first spray unit, a signal instructing spraying of an aromatic substance from the proximity of the doorway 104 toward the first room 101. When receiving the signal from the scattering direction switching unit 122, the first spray unit sprays an aromatic substance toward the advancing direction of the user 106 who enters the first room 101 from the second room 102. In a case where the second scattering direction from the proximity of the doorway 104 toward the second room 102 is determined as a scattering direction, the scattering direction switching unit 122 transmits, to the second spray unit, a signal instructing spraying of an aromatic substance from the proximity of the doorway 104 toward the second room 102. When receiving the signal from the scattering direction switching unit 122, the second spray unit sprays an aromatic substance toward the advancing direction of the user 106 who enters the second room 102 from the first room 101.

Also in the first embodiment, as disclosed in Japanese Unexamined Patent Publication No. 2015-136698, liquid stored in the storage unit 136 may be sprayed using a spring.

Second Embodiment

A scattering device in a second embodiment changes a kind of liquid, powder, or gas to be scattered according to current time.

Figure 7:
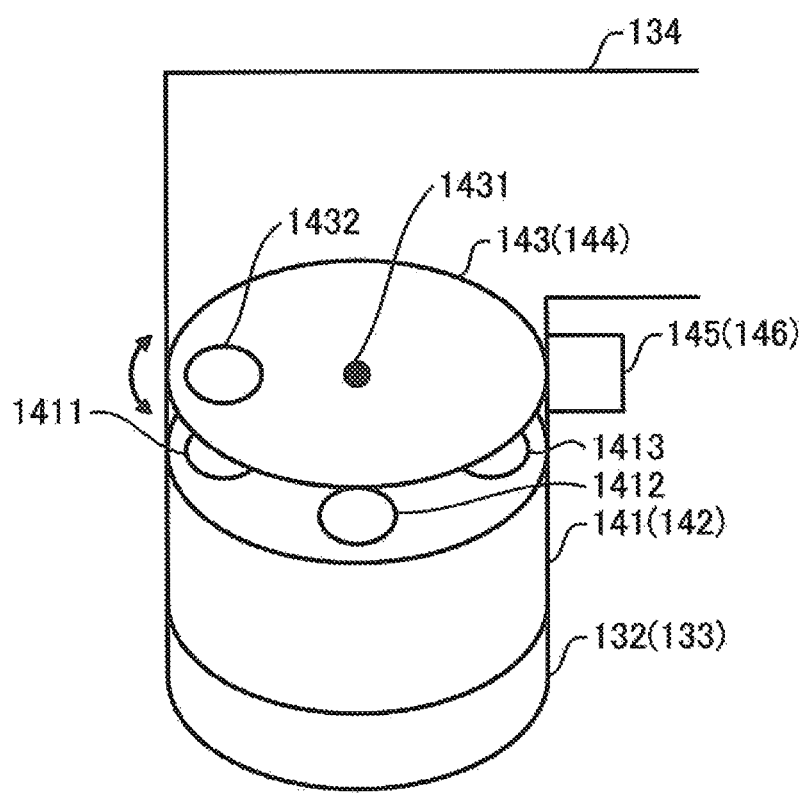
FIG. 7 is a view showing a configuration of a first storage unit of a scattering unit in a second embodiment of the present disclosure.
Figure 8:
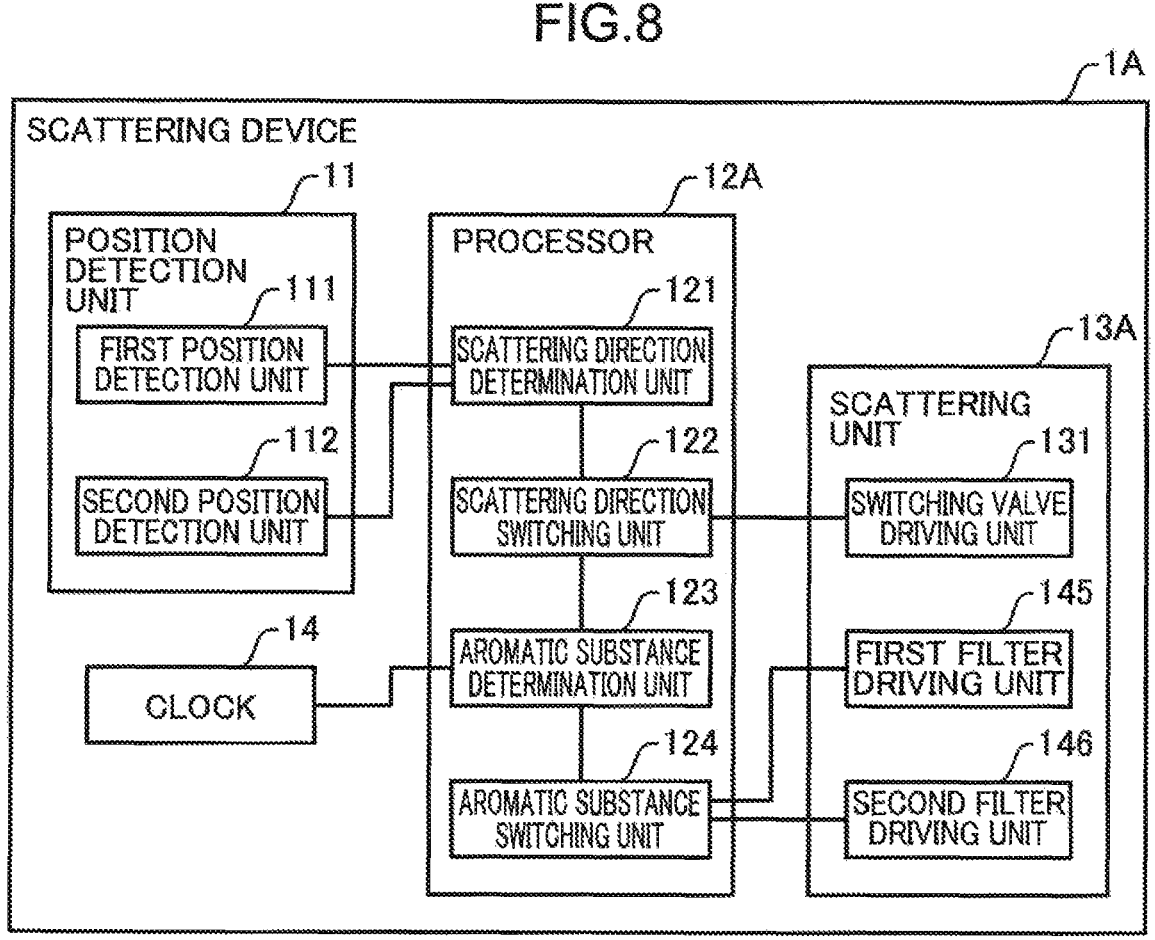
FIG. 8 is a block diagram showing a configuration of the scattering device in the second embodiment of the present disclosure.

FIG. 7 is a view showing a configuration of a first storage unit of a scattering unit in the second embodiment of the present disclosure, and FIG. 8 is a block diagram showing a configuration of the scattering device in the second embodiment of the present disclosure. In the second embodiment, the same configuration as in the first embodiment is given the same reference numeral to omit description thereof.

A scattering device 1A in the second embodiment includes a position detection unit 11, a processor 12A, a scattering unit 13A, and a clock 14.

The processor 12A, which is configured by, for example, a central processing unit, includes a scattering direction determination unit 121, a scattering direction switching unit 122, an aromatic substance determination unit 123, and an aromatic substance switching unit 124.

The aromatic substance determination unit 123 acquires current time from the clock 14. The aromatic substance determination unit 123 determines a kind of liquid, powder, or gas according to current time. In the second embodiment, liquid, powder, or gas to be scattered is an aromatic substance. In the second embodiment, the scattering device 1A scatters different kinds of aromatic substances in a morning time zone and an afternoon time zone. A memory (not shown) of the scattering device 1A may store in advance a kind of aromatic substance to be scattered in the morning time zone and a kind of aromatic substance to be scattered in the afternoon time zone. The aromatic substance determination unit 123 determines whether current time is in the morning time zone or in the afternoon time zone. When determining that the current time is in the morning time zone, the aromatic substance determination unit 123 determines a kind of aromatic substance correlated with the morning time zone as a kind of aromatic substance to be scattered. Also, when determining that the current time is in the afternoon time zone, the aromatic substance determination unit 123 determines a kind of aromatic substance correlated with the afternoon time zone as a kind of aromatic substance to be scattered.

The aromatic substance switching unit 124 switches a kind of aromatic substance to be scattered to a kind of aromatic substance determined by the aromatic substance determination unit 123. The aromatic substance switching unit 124 outputs, to one of a first filter driving unit 145 and a second filter driving unit 146, the aromatic substance switching signal for switching a kind of aromatic substance to be scattered to a kind of aromatic substance determined by the aromatic substance determination unit 123. In a case where the first scattering direction is determined as the scattering direction by the scattering direction determination unit 121, the aromatic substance switching unit 124 outputs the aromatic substance switching signal to the first filter driving unit 145. By contrast, in a case where the second scattering direction is determined as the scattering direction by the scattering direction determination unit 121, the aromatic substance switching unit 124 outputs the aromatic substance switching signal to the second filter driving unit 146.

The scattering unit 13A in the second embodiment includes a switching valve driving unit 131, a first scattering opening 132, a second scattering opening 133, a duct 134, a pump 135, a switching valve 137, a first storage unit 141, a second storage unit 142, a first filter 143, a second filter 144, the first filter driving unit 145, and the second filter driving unit 146.

The first storage unit 141 is provided between the switching valve 137 and the first scattering opening 132 and stores a plurality of liquids, powders, or gases of different kinds. The first storage unit 141 has, for example, a columnar shape and includes a first storage container 1411 which stores a first kind of liquid, powder, or gas, a second storage container 1412 which stores a second kind of liquid, powder, or gas, and a third storage container 1413 which stores a third kind of liquid, powder, or gas. Each of the first storage container 1411, the second storage container 1412, and the third storage container 1413 sends out liquid, powder, or gas as a result of passing of air sent from the pump 135.

The second storage unit 142 is provided between the switching valve 137 and the second scattering opening 133 to store a plurality of liquids, powders, or gases of different kinds. The second storage unit 142 has the same configuration as a configuration of the first storage unit 141.

The first filter 143 has a circular shape and is in sliding contact with an upper surface of the first storage unit 141. For the purpose of description, FIG. 7 shows the first filter 143 and the first storage unit 141 being apart from each other. A rotation shaft 1431 is provided at the center of the first filter 143. By the rotation of the rotation shaft 1431, the first filter 143 rotates. The first filter 143 has a circular opening portion 1432. The opening portion 1432 has the same shape and size as those of the first storage container 1411, the second storage container 1412, and the third storage container 1413. By the rotation of the first filter 143, the opening portion 1432 moves to a part above any of the first storage container 1411, the second storage container 1412, and the third storage container 1413. The first filter 143 limits a position through which air sent from the pump 135 passes by the opening portion 1432.

The second filter 144 has a circular shape and is in sliding contact with an upper surface of the second storage unit 142. The second filter 144 has the same configuration as that of the first filter 143.

A memory (not shown) of the scattering device 1A may store in advance a kind of aromatic substance stored in each of the first storage container 1411, the second storage container 1412, and the third storage container 1413.

The first filter driving unit 145 causes the first filter 143 to rotate by rotating the rotation shaft 1431 of the first filter 143. The first filter driving unit 145 causes the first filter 143 to rotate based on the aromatic substance switching signal output from the aromatic substance switching unit 124. For example, in a case of switching to the first kind of aromatic substance, the first filter driving unit 145 causes the first filter 143 to rotate such that the opening portion 1432 is positioned above the first storage container 1411. As a result, air sent from the pump 135 passes only through the first storage container 1411, so that the first kind of aromatic substance is sent out from the first storage container 1411.

The second filter driving unit 146 causes the second filter 144 to rotate by rotating the rotation shaft 1431 of the second filter 144. The second filter driving unit 146 causes the second filter 144 to rotate based on the aromatic substance switching signal output from the aromatic substance switching unit 124. The second filter driving unit 146 has the same configuration as that of the first filter driving unit 145.

Subsequently, operation of the scattering device 1A in the second embodiment will be described.

Figure 9:
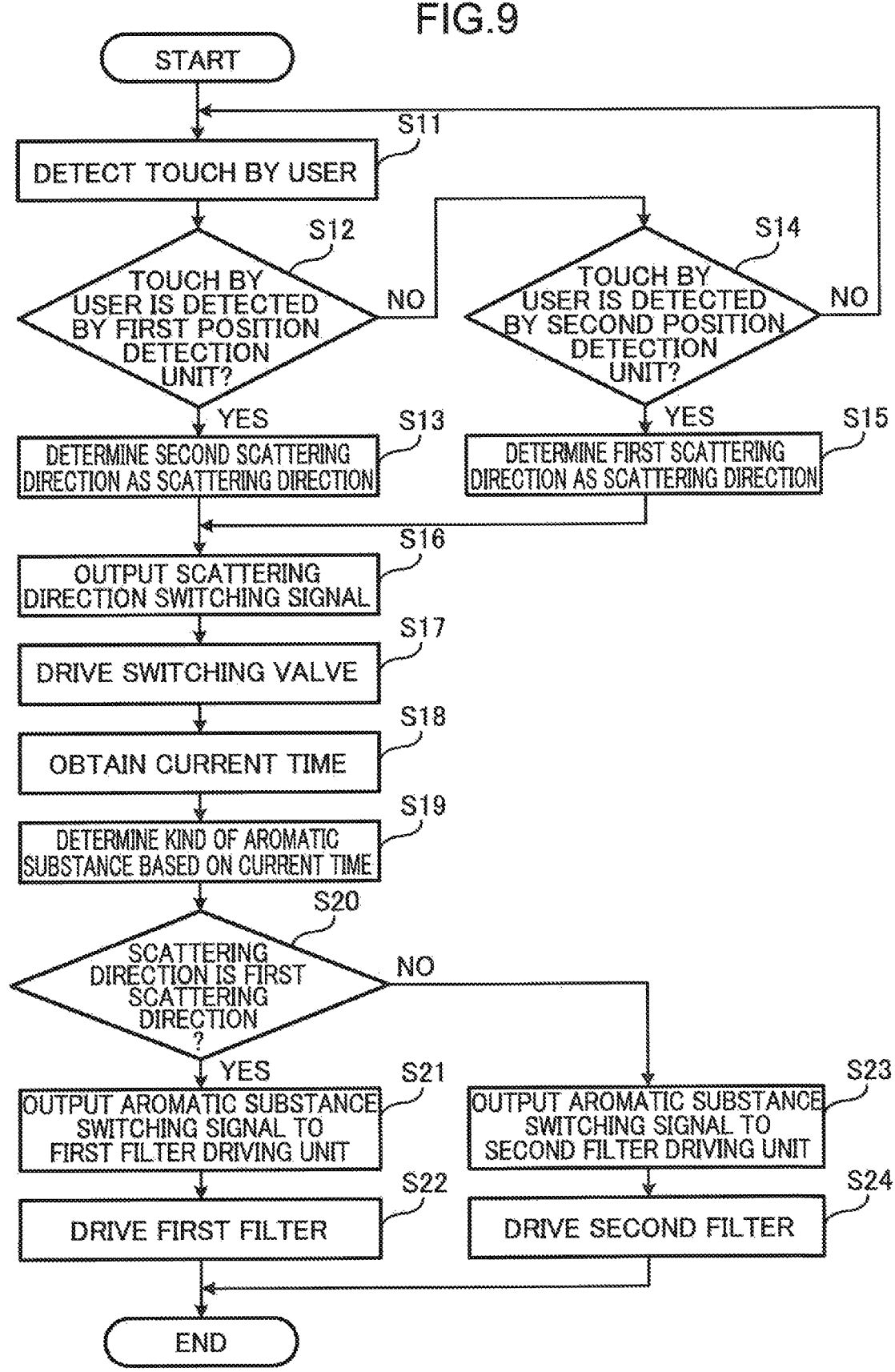
FIG. 9 is a flow chart for describing operation of the scattering device in the second embodiment of the present disclosure.

FIG. 9 is a flow chart for describing operation of the scattering device in the second embodiment of the present disclosure.

Since processing in Step S11 to Step S17 is the same as the processing in Step S1 to Step S7 shown in FIG. 6, description thereof will be omitted.

Next, in Step S18, the aromatic substance determination unit 123 obtains current time from the clock 14.

Next, in Step S19, the aromatic substance determination unit 123 determines a kind of aromatic substance based on the obtained current time. More specifically, the aromatic substance determination unit 123 determines whether or not the obtained current time is in the morning time zone. When determining that the current time is in the morning time zone, the aromatic substance determination unit 123 determines a kind of aromatic substance correlated with the morning time zone as a kind of aromatic substance to be scattered. When determining that the current time is not in the morning time zone, i.e., when determining that the current time is in the afternoon time zone, the aromatic substance determination unit 123 determines a kind of aromatic substance correlated with the afternoon time zone as a kind of aromatic substance to be scattered.

Next, in Step S20, the aromatic substance switching unit 124 determines whether or not the scattering direction determined by the scattering direction determination unit 121 is the first scattering direction.

Here, when determination is made that the scattering direction is the first scattering direction (YES in Step S20), the aromatic substance switching unit 124 in Step S21 outputs, to the first filter driving unit 145, the aromatic substance switching signal for switching a kind of aromatic substance to be scattered to the kind of aromatic substance determined by the aromatic substance determination unit 123.

Next, in Step S22, the first filter driving unit 145 drives the first filter 143 based on the aromatic substance switching signal output from the aromatic substance switching unit 124. The first filter driving unit 145 causes the opening portion 1432 of the first filter 143 to move to a position corresponding to a storage container in which the kind of aromatic substance determined by the aromatic substance determination unit 123 is stored among the plurality of storage containers.

By contrast, when determination is made that the scattering direction is not the first scattering direction, i.e., when determination is made that the scattering direction is the second scattering direction (NO in Step S20), the aromatic substance switching unit 124 in Step S23 outputs, to the second filter driving unit 146, the aromatic substance switching signal for switching a kind of aromatic substance to be scattered to the kind of aromatic substance determined by the aromatic substance determination unit 123.

Next, in Step S24, the second filter driving unit 146 drives the second filter 144 based on the aromatic substance switching signal output from the aromatic substance switching unit 124. The second filter driving unit 146 causes the opening portion 1432 of the second filter 144 to move to a position corresponding to a storage container in which the kind of aromatic substance determined by the aromatic substance determination unit 123 is stored among the plurality of storage containers.

By thus changing a kind of liquid, powder, or gas in, for example, the morning time zone and the afternoon time zone, the user 106 is allowed to recognize time change by a change of liquid, powder, or gas to be scattered.

While in the second embodiment, the aromatic substance determination unit 123 changes a kind of aromatic substance to be scattered according to current time, the present disclosure is not particularly limited thereto, and whether or not to scatter an aromatic substance may be determined according to current time. For example, the aromatic substance determination unit 123 may determine not to scatter an aromatic substance when the current time is in a predetermined time zone and may determine to scatter an aromatic substance when the current time is outside the predetermined time zone. The predetermined time zone may be, for example, a time zone for meal, a time zone from 11 to 12 o'clock.

Third Embodiment

A scattering device in the third embodiment measures a load applied on a door when a user opens the door, specifies user's gender and age according to the measured load, identifies a user who has opened the door from the specified gender and age, and scatters a kind of aromatic substance correlated with the identified user.

Figure 10:
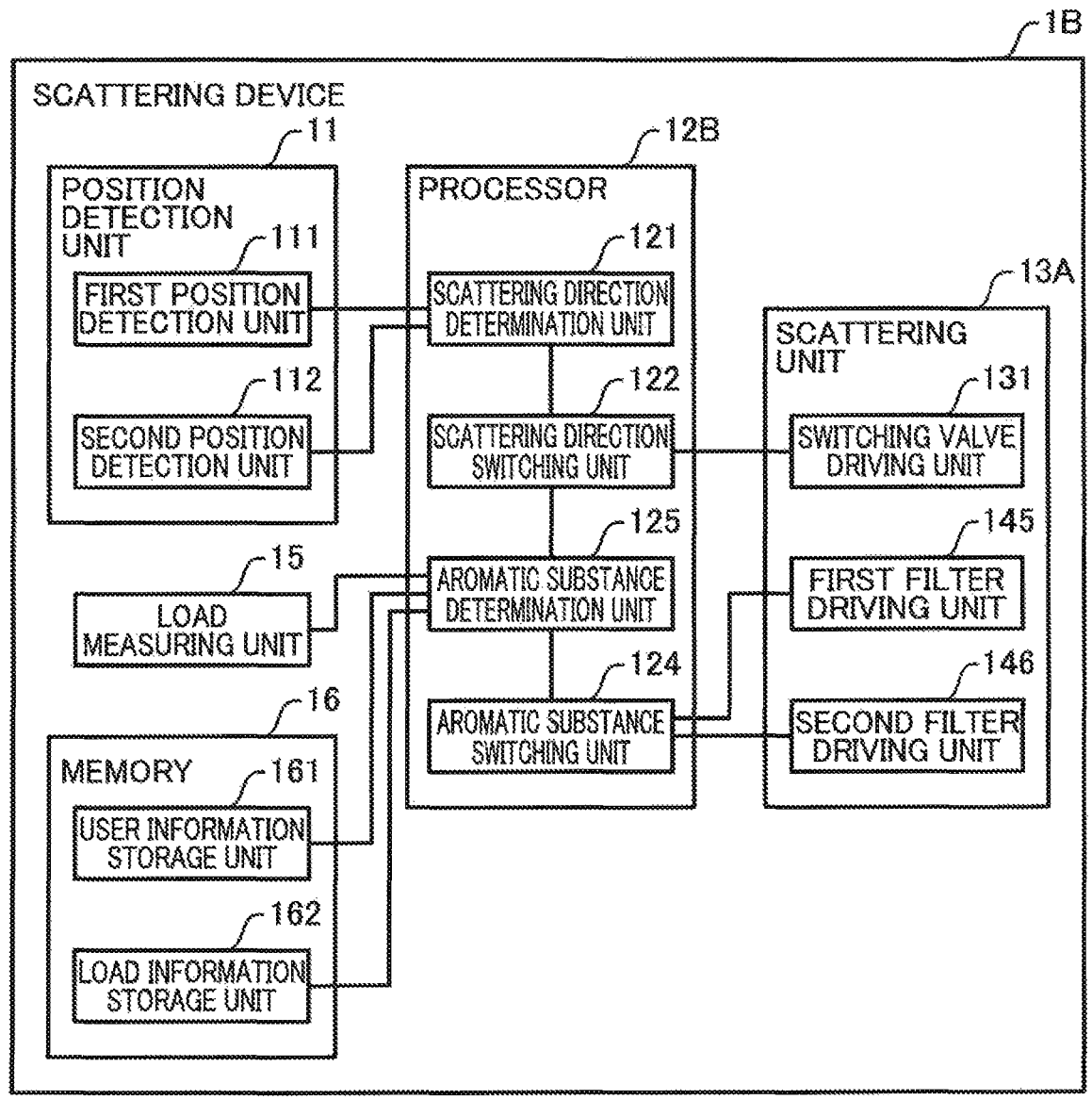
FIG. 10 is a block diagram showing a configuration of a scattering device in a third embodiment of the present disclosure.

FIG. 10 is a block diagram showing a configuration of the scattering device in the third embodiment of the present disclosure. In the third embodiment, the same configuration as in the first and second embodiments is given the same reference numeral to omit description thereof.

A scattering device 1B in the third embodiment includes a position detection unit 11, a processor 12B, a scattering unit 13A, a load measuring unit 15, and a memory 16.

The processor 12B, which is configured by, for example, a central processing unit, includes a scattering direction determination unit 121, a scattering direction switching unit 122, an aromatic substance switching unit 124, and an aromatic substance specifying unit 125. The memory 16 includes a user information storage unit 161 and a load information storage unit 162.

The user information storage unit 161 stores user information which correlates identification information for identifying a user, age of the user, gender of the user, and a kind of liquid, powder, or gas. Liquid, powder, or gas in the third embodiment is an aromatic substance. The identification information is information for identifying each family member living in a house in which the scattering device 1B is installed.

The load information storage unit 162 stores in advance load information indicative of a relationship between a load applied on a door when a male opens the door and his age and also indicative of a load applied on a door when a female opens the door and her age. There is a correlation between a load applied on a door when a person opens the door and age and gender of the person. Therefore, when a person opens a door, age and gender of the person can be estimated from the load applied on the door.

The load measuring unit 15 measures a load applied on a door 105 when a user 106 opens the door 105. In a case where the door 105 is of a hinged door type, the load measuring unit 15 may measure a load applied on a hinge for attaching the door 105 to a wall 103 as a load applied on the door 105 when the user 106 opens the door 105. In a case where the door 105 is of a sliding door type, the load measuring unit 15 may measure a load applied on a roller provided on an upper portion of the door 105 or a guide pin provided on a lower portion of the door 105 as a load applied on the door 105 when the user 106 opens the door 105.

The aromatic substance specifying unit 125 estimates user's age and gender corresponding to the load measured by the load measuring unit 15. Specifically, the aromatic substance specifying unit 125 refers to the load information stored in the load information storage unit 162 to estimate user's age and gender corresponding to the load measured by the load measuring unit 15.

The aromatic substance specifying unit 125 refers to the user information stored in the user information storage unit 161 to specify a kind of liquid, powder, or gas correlated with estimated age and gender. Specifically, the aromatic substance specifying unit 125 refers to the user information stored in the user information storage unit 161 to specify a kind of aromatic substance correlated with estimated age and gender.

The memory 16 may store in advance an estimation model obtained by machine learning with a load applied on a door when a person opens the door as an input and age and gender as an output. Then, the aromatic substance specifying unit 125 may input a load measured by the load measuring unit 15 to the estimation model to obtain age and gender output from the estimation model as an estimation result.

The aromatic substance switching unit 124 switches a kind of aromatic substance to be scattered to a kind of aromatic substance specified by the aromatic substance specifying unit 125.

Subsequently, operation of the scattering device 1B in the third embodiment will be described.

Figure 11:
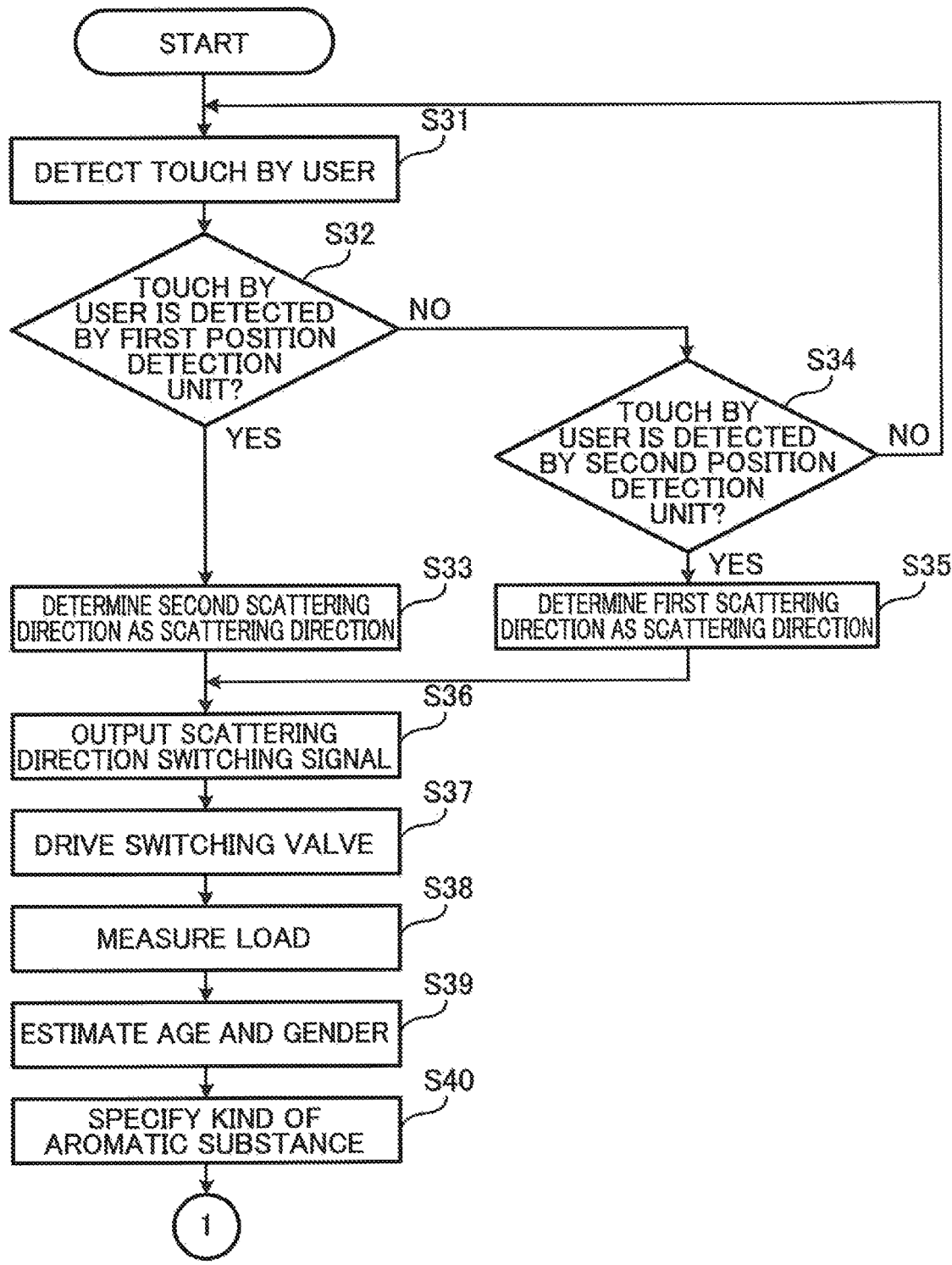
FIG. 11 is a first flow chart for describing operation of the scattering device in the third embodiment of the present disclosure.
Figure 12:
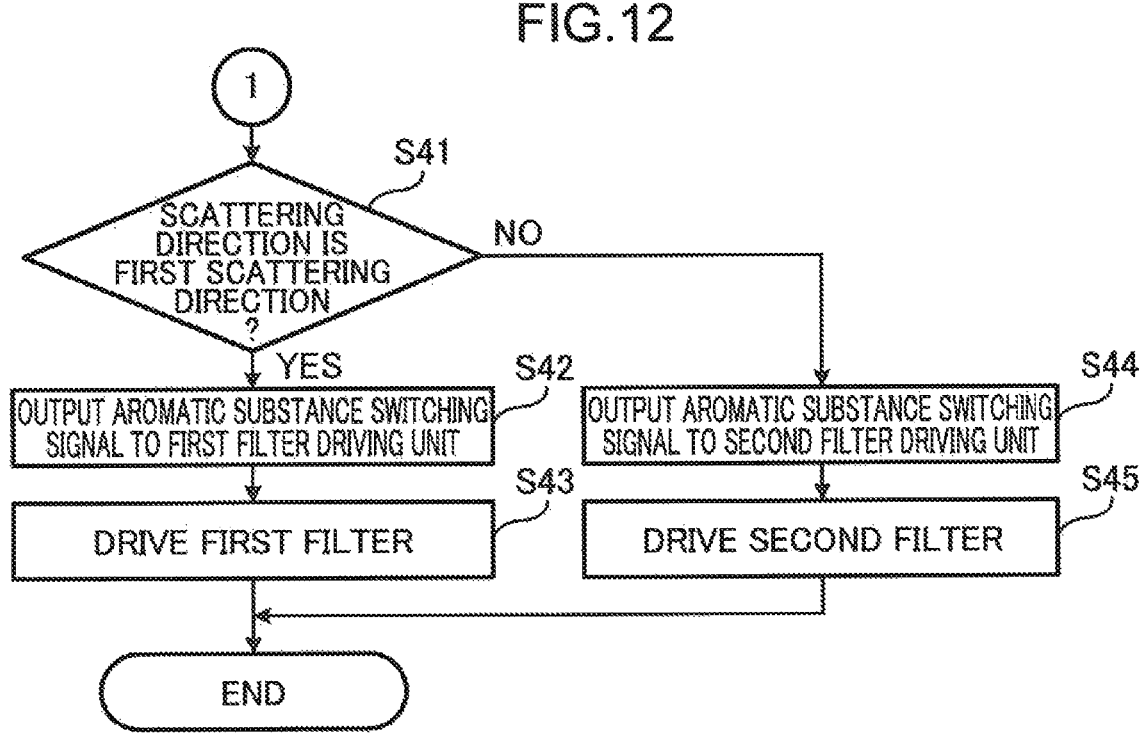
FIG. 12 is a second flow chart for describing operation of the scattering device in the third embodiment of the present disclosure.

FIG. 11 is a first flow chart for describing operation of the scattering device in the third embodiment of the present disclosure, and FIG. 12 is a second flow chart for describing operation of the scattering device in the third embodiment of the present disclosure;

Since processing in Step S31 to Step S37 is the same as the processing in Step S1 to Step S7 shown in FIG. 6, description thereof will be omitted.

Next, in Step S38, the load measuring unit 15 measures a load applied on the door 105 when the user 106 opens the door 105.

Next, in Step S39, the aromatic substance specifying unit 125 refers to the load information stored in the load information storage unit 162 to estimate age and gender corresponding to the load measured by the load measuring unit 15.

Next, in Step S40, the aromatic substance specifying unit 125 refers to the user information stored in the user information storage unit 161 to specify a kind of aromatic substance correlated with the estimated age and gender.

Next, in Step S41, the aromatic substance switching unit 124 determines whether or not the scattering direction determined by the scattering direction determination unit 121 is the first scattering direction.

Here, when determination is made that the scattering direction is the first scattering direction (YES in Step S41), the aromatic substance switching unit 124 in Step S42 outputs, to the first filter driving unit 145, the aromatic substance switching signal for switching a kind of aromatic substance to be scattered to the kind of aromatic substance specified by the aromatic substance specifying unit 125.

Since processing in Step S43 is the same as the processing in Step S22 shown in FIG. 9, description thereof will be omitted.

By contrast, when determination is made that the scattering direction is not the first scattering direction, i.e., when determination is made that the scattering direction is the second scattering direction (NO in Step S41), the aromatic substance switching unit 124 in Step S44 outputs, to the second filter driving unit 146, the aromatic substance switching signal for switching a kind of aromatic substance to be scattered to the kind of aromatic substance specified by the aromatic substance specifying unit 125.

Since processing in Step S45 is the same as the processing in Step S24 shown in FIG. 9, description thereof will be omitted.

Age and gender of the user 106 are thus estimated from a load applied on the door 105 when the user 106 opens the door 105, and a kind of liquid, powder, or gas desired by the user 106 is specified from the estimated age and gender. Accordingly, by opening of the door 105 by the user 106, liquid, powder, or gas of a kind desired by the user 106 who has opened the door 105 can be scattered.

While in the third embodiment, a load applied on the door 105 when the user 106 opens the door 105 is measured and gender and age of the user 106 are estimated from the measured load to specify a kind of aromatic substance corresponding to the estimated gender and age, the present disclosure is not particularly limited thereto. The scattering device 1B may further include a camera which captures an image of a face of the user 106 opening the door 105. The user information storage unit 161 may store the user information which correlates the identification information for identifying a user, a face image of the user, and a kind of aromatic substance. Then, the aromatic substance specifying unit 125 may refer to the user information stored in the user information storage unit 161 to specify a kind of aromatic substance correlated with the face image of the user 106 captured by the camera.

Also in the third embodiment, the scattering device 1B may include a communication unit. For example, the communication unit may obtain, from the outside, the user information and the load information accumulated in the memory 16 shown in FIG. 10 to update the user information and the load information in the memory 16.

Fourth Embodiment

A scattering device in the fourth embodiment measures a load applied on a door when a user opens the door, measures an acceleration of the door when the user opens the door, inputs the load and the acceleration to a prediction model obtained by machine learning, predicts emotion output from the prediction model as user's emotion when the user opens the door, and scatters a kind of aromatic substance correlated with the predicted user's emotion.

Figure 13:
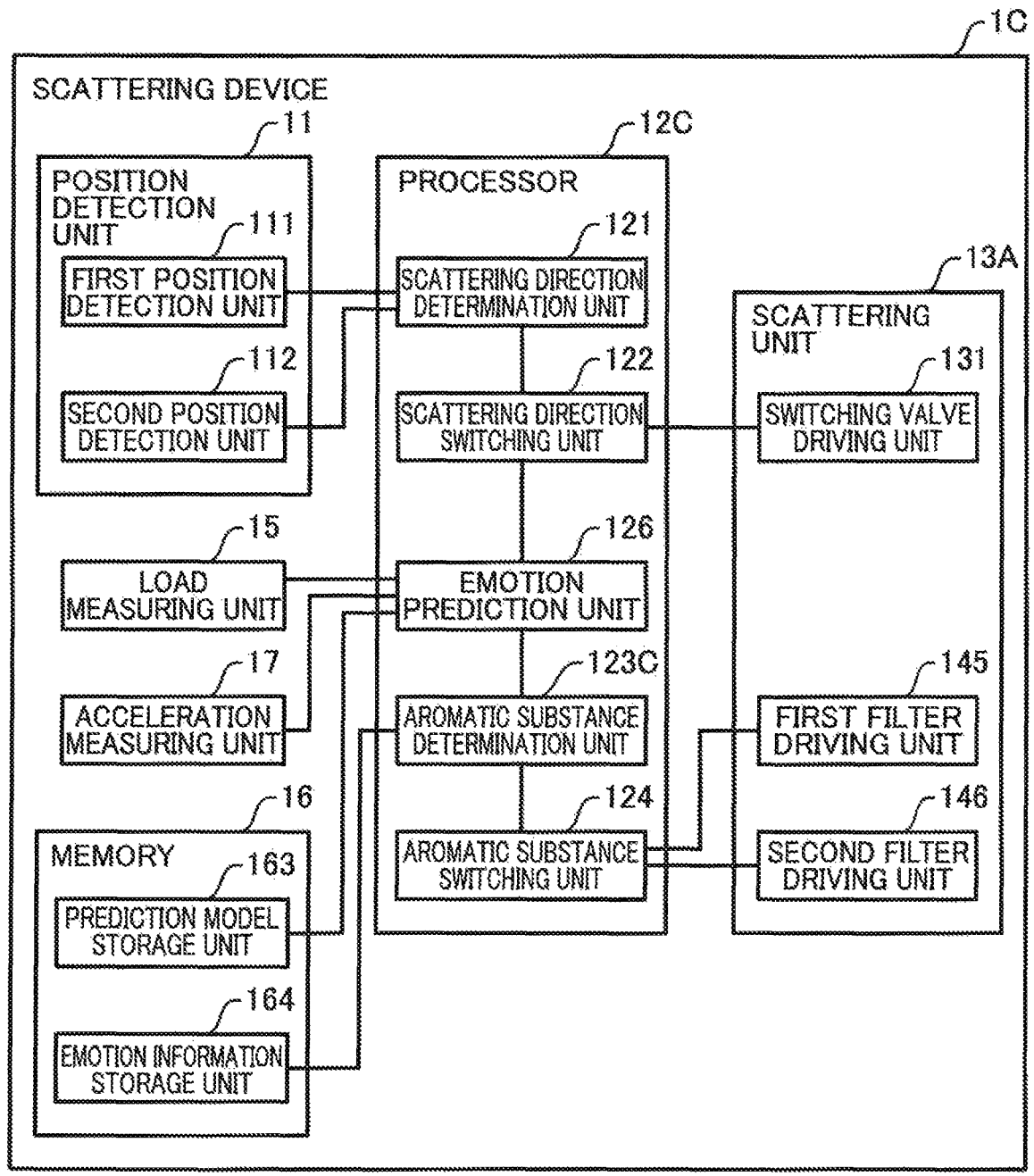
FIG. 13 is a block diagram showing a configuration of a scattering device in a fourth embodiment of the present disclosure.

FIG. 13 is a block diagram showing a configuration of the scattering device in the fourth embodiment of the present disclosure. In the fourth embodiment, the same configuration as in the first to third embodiments is given the same reference numeral to omit description thereof.

A scattering device 1C in the fourth embodiment includes a position detection unit 11, a processor 12C, a scattering unit 13A, a load measuring unit 15, a memory 16, and an acceleration measuring unit 17.

The processor 12C, which is configured by, for example, a central processing unit, includes a scattering direction determination unit 121, a scattering direction switching unit 122, an aromatic substance determination unit 123C, an aromatic substance switching unit 124, and an emotion prediction unit 126. The memory 16 includes a prediction model storage unit 163 and an emotion information storage unit 164.

The acceleration measuring unit 17 measures an acceleration of the door 105 when the user 106 opens the door 105. The acceleration measuring unit 17 is arranged at the door 105.

The prediction model storage unit 163 stores in advance a prediction model obtained by machine learning using teaching data with a load applied on a door when the user 106 opens the door 105 and an acceleration of the door 105 when the user 106 opens the door 105 as input data and emotion of the user 106 as output data. Emotion of the user 106 may be, for example, any emotion of "joy", "anger", "pity", and "ease". Emotion of the user 106 may be, for example, either emotion with anger or emotion without anger.

The emotion information storage unit 164 stores in advance emotion information which correlates emotion of the user 106 with a kind of aromatic substance. For example, anger emotion is correlated with an aromatic substance having scent which relaxes person's mind.

The emotion prediction unit 126 inputs, to the prediction model stored in the prediction model storage unit 163, a load measured by the load measuring unit 15 and an acceleration measured by the acceleration measuring unit 17 to predict emotion output from the prediction model as emotion of the user 106 when the user 106 opens the door 105.

The aromatic substance determination unit 123C determines a kind of liquid, powder, or gas according to emotion predicted by the emotion prediction unit 126. In the fourth embodiment, liquid, powder, or gas to be scattered is an aromatic substance. Specifically, the aromatic substance determination unit 123C refers to the emotion information stored in the emotion information storage unit 164 to specify a kind of aromatic substance correlated with the emotion predicted by the emotion prediction unit 126.

The aromatic substance switching unit 124 switches a kind of aromatic substance to be scattered to a kind of aromatic substance determined by the aromatic substance determination unit 123C.

Subsequently, operation of the scattering device 1C in the fourth embodiment will be described.

Figure 14:
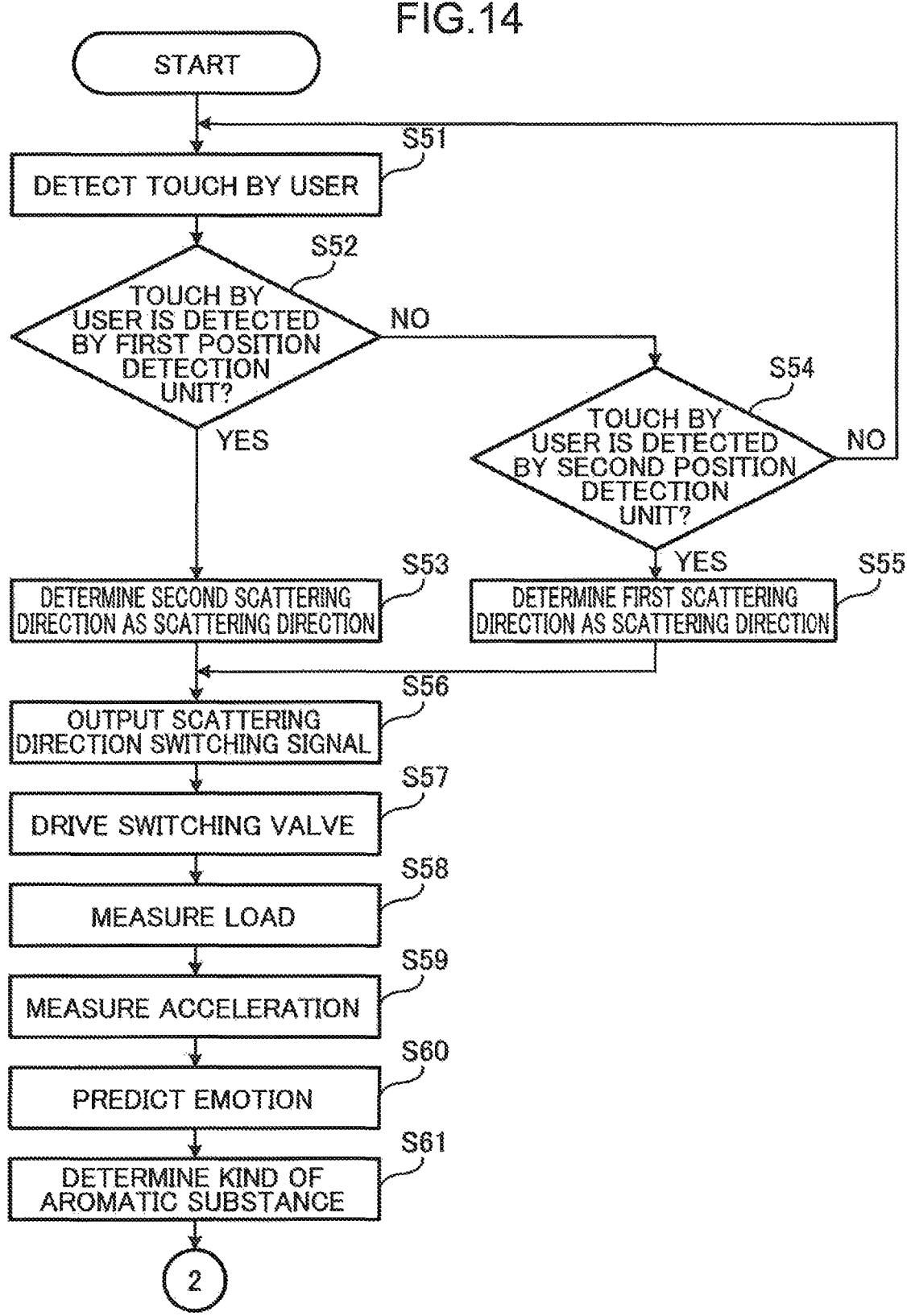
FIG. 14 is a first flow chart for describing operation of the scattering device in the fourth embodiment of the present disclosure.
Figure 15:
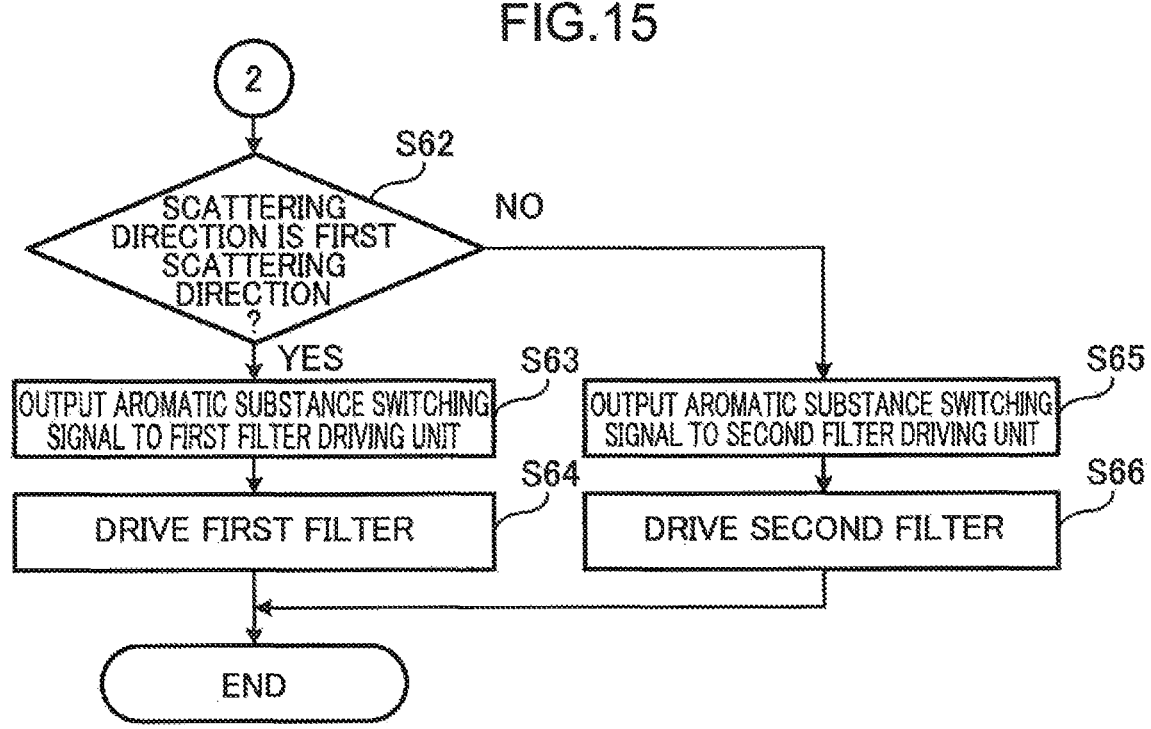
FIG. 15 is a second flow chart for describing operation of the scattering device in the fourth embodiment of the present disclosure.

FIG. 14 is a first flow chart for describing operation of the scattering device in the fourth embodiment of the present disclosure, and FIG. 15 is a second flow chart for describing operation of the scattering device in the fourth embodiment of the present disclosure.

Since processing in Step S51 to Step S57 is the same as the processing in Step S1 to Step S7 shown in FIG. 6, description thereof will be omitted.

Next, in Step S58, the load measuring unit 15 measures a load applied on the door 105 when the user 106 opens the door 105.

Next, in Step S59, the acceleration measuring unit 17 measures an acceleration of the door 105 when the user 106 opens the door 105.

Next, in Step S60, the emotion prediction unit 126 inputs, to the prediction model stored in the prediction model storage unit 163, a load measured by the load measuring unit 15 and an acceleration measured by the acceleration measuring unit 17 to predict emotion output from the prediction model as emotion of the user 106 when the user 106 opens the door 105.

Next, in Step S61, the aromatic substance determination unit 123C refers to the emotion information stored in the emotion information storage unit 164 to determine a kind of aromatic substance correlated with the emotion predicted by the emotion prediction unit 126 as a kind of aromatic substance to be scattered.

Since processing in Step S62 to Step S66 is the same as the processing in Step S20 to Step S24 shown in FIG. 9, description thereof will be omitted.

In this manner, emotion of the user 106 when the user 106 opens the door 105 is predicted from a load applied on the door 105 when the user 106 opens the door 105 and an acceleration of the door 105 when the user 106 opens the door 105 to determine a kind of liquid, powder, or gas according to the predicted emotion. Accordingly, by opening the door 105 by the user 106, a kind of liquid, powder, or gas corresponding to emotion of the user 106 who opened the door 105 can be scattered.

While in the fourth embodiment, the emotion prediction unit 126 predicts emotion of the user 106 by using a load measured by the load measuring unit 15 and an acceleration measured by the acceleration measuring unit 17, the present disclosure is not particularly limited thereto, and emotion of the user 106 may be predicted by using only a load measured by the load measuring unit 15 or emotion of the user 106 may be predicted by using only an acceleration measured by the acceleration measuring unit 17.

Also in the fourth embodiment, the scattering device 1C may further include a camera which captures an image of a face of the user 106 opening the door 105. The prediction model storage unit 163 may store in advance a prediction model obtained by machine learning using teaching data with a face image of the user 106 when the user 106 opens the door 105 as input data and emotion of the user 106 as output data. Then, the emotion prediction unit 126 may input a face image of the user 106 captured by the camera to the prediction model stored in the prediction model storage unit 163 to predict emotion output from the prediction model as emotion of the user 106 when the user 106 opens the door 105.

Also in the fourth embodiment, the scattering device 1C may further include a biosensor which measures bioinformation of the user 106 who opens the door 105. The bioinformation is, for example, at least one of a body motion, a heart rate, and a respiration rate of the user 106. The prediction model storage unit 163 may store in advance a prediction model obtained by machine learning using teaching data with bioinformation of the user 106 when the user 106 opens the door 105 as input data and emotion of the user 106 as output data. Then, the emotion prediction unit 126 may input, to the prediction model stored in the prediction model storage unit 163, bioinformation of the user 106 measured by the biosensor to predict emotion output from the prediction model as emotion of the user 106 when the user 106 opens the door 105.

Also in the fourth embodiment, the scattering device 1C may include a communication unit. For example, the communication unit may obtain, from the outside, the prediction model and the emotion information accumulated in the memory 16 shown in FIG. 13 to update the prediction model and the emotion information in the memory 16.

Fifth Embodiment

A scattering device in the fifth embodiment measures an odor concentration in a first space when a user moves from the first space to a second space, determines a scatter amount of liquid, powder, or gas to be scattered in a direction from a proximity of a doorway toward the second space according to the odor concentration of the first space, and scatters the determined scatter amount of liquid, powder, or gas.

Figure 16:
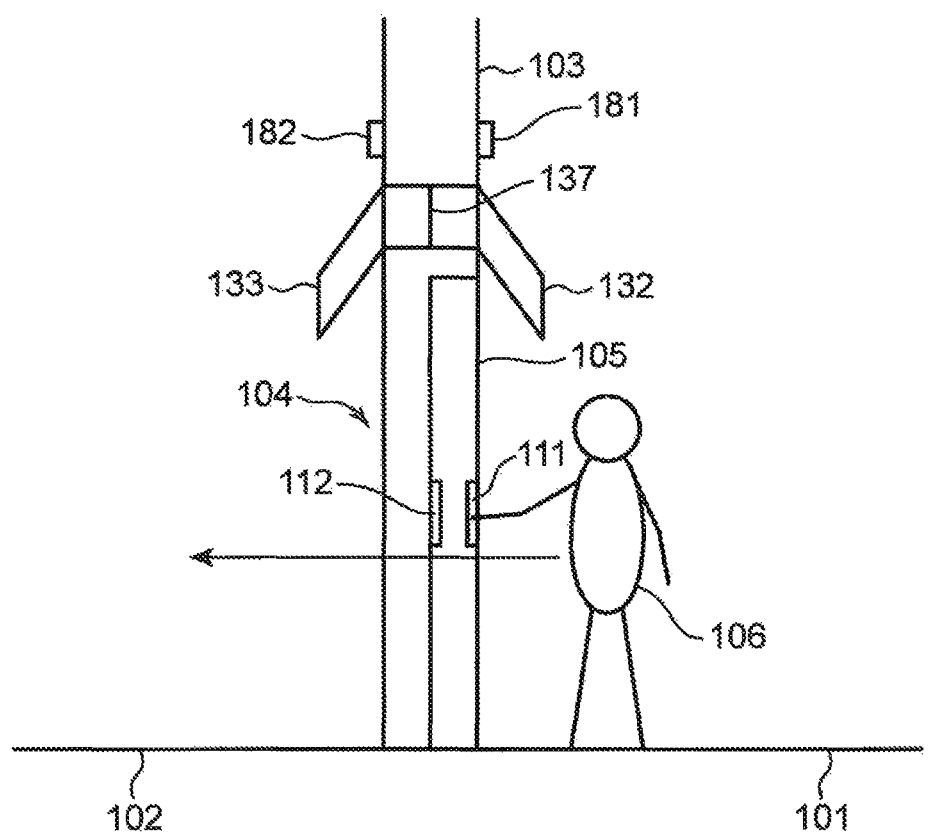
FIG. 16 is a view of a doorway seen from the side in a fifth embodiment of the present disclosure.
Figure 17:
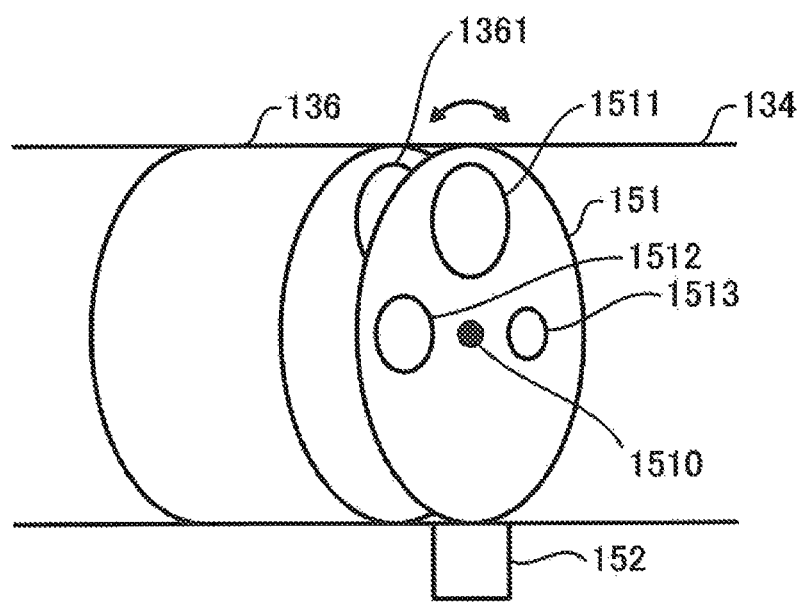
FIG. 17 is a view showing a configuration of a filter of a scattering unit and a filter driving unit in the fifth embodiment of the present disclosure.
Figure 18:
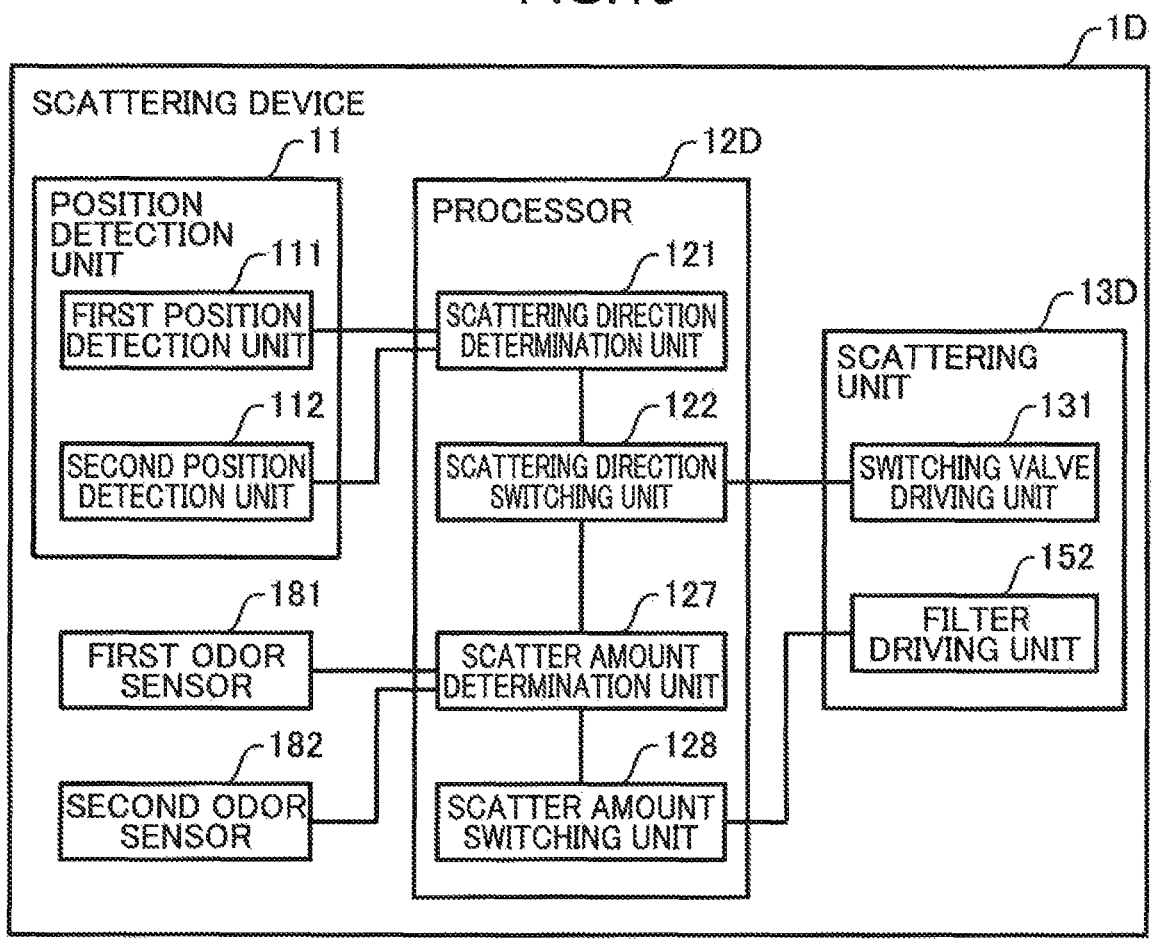
FIG. 18 is a block diagram showing a configuration of the scattering device in the fifth embodiment of the present disclosure.

FIG. 16 is a view of the doorway seen from the side in the fifth embodiment of the present disclosure, FIG. 17 is a view showing a configuration of a filter of a scattering unit and a filter driving unit in the fifth embodiment of the present disclosure, and FIG. 18 is a block diagram showing a configuration of the scattering device in the fifth embodiment of the present disclosure. In the fifth embodiment, the same configuration as in the first to fourth embodiments is given the same reference numeral to omit description thereof.

A scattering device 1D in the fifth embodiment includes a position detection unit 11, a processor 12D, a scattering unit 13D, a first odor sensor 181, and a second odor sensor 182.

The processor 12D, which is configured by, for example, a central processing unit, includes a scattering direction determination unit 121, a scattering direction switching unit 122, a scatter amount determination unit 127, and a scatter amount switching unit 128.

As shown in FIG. 16, the first odor sensor 181 is arranged above a doorway 104 of a first room 101. The first odor sensor 181 measures an odor concentration in the first room 101.

As shown in FIG. 16, the second odor sensor 182 is arranged above the doorway 104 of a second room 102. The second odor sensor 182 measures an odor concentration in the second room 102.

When a user 106 moves from the first room 101 to the second room 102, the scatter amount determination unit 127 determines a scatter amount of liquid, powder, or gas to be scattered in a direction from the proximity of the doorway 104 toward the second room 102 according to an odor concentration of the first room 101 measured by the first odor sensor 181. In the fifth embodiment, liquid, powder, or gas to be scattered is an aromatic substance.

For example, in a case where the first room 101 has a high odor concentration when the user 106 moves from the first room 101 to the second room 102, if the scatter amount of aromatic substance to be scattered in a direction from the proximity of the doorway 104 toward the second room 102 is small, the user 106 can hardly sense odor of the aromatic substance. Therefore, in the case where the first room 101 has a high odor concentration when the user 106 moves from the first room 101 to the second room 102, the scatter amount of aromatic substance to be scattered in the direction from the proximity of the doorway 104 toward the second room 102 is increased to be larger than usual.

In a case where the first room 101 has a low odor concentration when the user 106 moves from the first room 101 to the second room 102, even if the scatter amount of aromatic substance to be scattered in the direction from the proximity of the doorway 104 toward the second room 102 is small, the user 106 can satisfactorily sense scent of the aromatic substance. Therefore, in the case where the first room 101 has a low odor concentration when the user 106 moves from the first room 101 to the second room 102, the scatter amount of aromatic substance to be scattered in the direction from the proximity of the doorway 104 toward the second room 102 can be reduced to be smaller than usual.

In the fifth embodiment, the scatter amount is changeable in, for example, three stages. The scatter amount determination unit 127 determines any of a first scatter amount, a second scatter amount smaller than the first scatter amount, and a third scatter amount smaller than the second scatter amount. In a case where the user 106 is detected in the first room 101 and the odor concentration of the first room 101 measured by the first odor sensor 181 is higher than a first threshold value, the scatter amount determination unit 127 determines the scatter amount of aromatic substance to be scattered in the direction from the proximity of the doorway 104 toward the second room 102 as the first scatter amount. In a case where the user 106 is detected in the first room 101 and the odor concentration of the first room 101 measured by the first odor sensor 181 is lower than a second threshold value, the scatter amount determination unit 127 determines the scatter amount of aromatic substance to be scattered in the direction from the proximity of the doorway 104 toward the second room 102 as a third scatter amount. The second threshold value is smaller than the first threshold value. Further, in a case where the user 106 is detected in the first room 101 and the odor concentration of the first room 101 measured by the first odor sensor 181 is between the first threshold value and the second threshold value, the scatter amount determination unit 127 determines the scatter amount of aromatic substance to be scattered in the direction from the proximity of the doorway 104 toward the second room 102 as the second scatter amount.

Also, when the user 106 moves from the second room 102 to the first room 101, the scatter amount determination unit 127 determines a scatter amount of liquid, powder, or gas to be scattered in the direction from the proximity of the doorway 104 toward the first room 101 according to an odor concentration of the second room 102 measured by the second odor sensor 182.

The scatter amount switching unit 128 switches a scatter amount of an aromatic substance to a scatter amount determined by the scatter amount determination unit 127. The scatter amount switching unit 128 outputs, to a filter driving unit 152, a scatter amount switching signal for switching a scatter amount of an aromatic substance to any one of the first scatter amount, the second scatter amount, and the third scatter amount determined by the scatter amount determination unit 127.

The scattering unit 13D in the fifth embodiment includes a switching valve driving unit 131, a first scattering opening 132, a second scattering opening 133, a duct 134, a pump 135, a switching valve 137, a storage unit 136, a filter 151, and the filter driving unit 152. Configuration, other than the filter 151 and the filter driving unit 152, of the scattering unit 13D in the fifth embodiment is the same as the configuration of the scattering unit 13 in the first embodiment.

As shown in FIG. 17, the storage unit 136 has, for example, a columnar shape and includes a storage container 1361 which stores liquid, powder, or gas. The storage container 1361 sends out liquid, powder, or gas as a result of passing of air sent from the pump 135.

The filter 151 is arranged between the pump 135 and the storage unit 136. The filter 151 has a circular shape and is in sliding contact with a face, on the pump 135 side, of the storage unit 136. For the purpose of description, FIG. 17 shows the filter 151 and the storage unit 136 being apart from each other. A rotation shaft 1510 is provided at the center of the filter 151. By the rotation of the rotation shaft 1510, the filter 151 rotates. The filter 151 has a first opening portion 1511, a second opening portion 1512, and a third opening portion 1513 which are all circular. The first opening portion 1511 has the same shape and size as those of the storage container 1361. The second opening portion 1512 has a diameter shorter than a diameter of the first opening portion 1511, and the third opening portion 1513 has a diameter shorter than a diameter of the second opening portion 1512.

By the rotation of the filter 151, the first opening portion 1511, the second opening portion 1512 or the third opening portion 1513 moves to the position of the storage container 1361. The filter 151 limits a passage amount of air sent from the pump 135 by the first opening portion 1511, the second opening portion 1512 or the third opening portion 1513 having different sizes. In a case where a scatter amount of an aromatic substance is switched to the first scatter amount as the largest amount, the first opening portion 1511 moves to the position of the storage container 1361. In a case where the scatter amount of an aromatic substance is switched to the second scatter amount which is smaller than the first scatter amount, the second opening portion 1512 moves to the position of the storage container 1361. Further, in a case where the scatter amount of an aromatic substance is switched to the third scatter amount which is smaller than the second scatter amount, the third opening portion 1513 moves to the position of the storage container 1361.

By rotating the rotation shaft 1510 of the filter 151, the filter driving unit 152 causes the filter 151 to rotate. The filter driving unit 152 causes the filter 151 to rotate based on the scatter amount switching signal output from the scatter amount switching unit 128.

For example, in a case of switching to the first scatter amount, the filter driving unit 152 causes the filter 151 to rotate such that the first opening portion 1511 is positioned in front of the storage container 1361. As a result, air sent from the pump 135 passes through the first opening portion 1511 and the storage container 1361, thereby sending out the first scatter amount of an aromatic substance from the storage container 1361.

In a case of switching to the second scatter amount, the filter driving unit 152 causes the filter 151 to rotate such that the second opening portion 1512 is positioned in front of the storage container 1361. As a result, air sent from the pump 135 passes through the second opening portion 1512 and the storage container 1361, thereby sending out the second scatter amount of an aromatic substance from the storage container 1361.

Further, in a case of switching to the third scatter amount, the filter driving unit 152 causes the filter 151 to rotate such that the third opening portion 1513 is positioned in front of the storage container 1361. As a result, air sent from the pump 135 passes through the third opening portion 1513 and the storage container 1361, thereby sending out the third scatter amount of an aromatic substance from the storage container 1361.

Subsequently, operation of the scattering device 1D in the fifth embodiment will be described.

Figure 19:
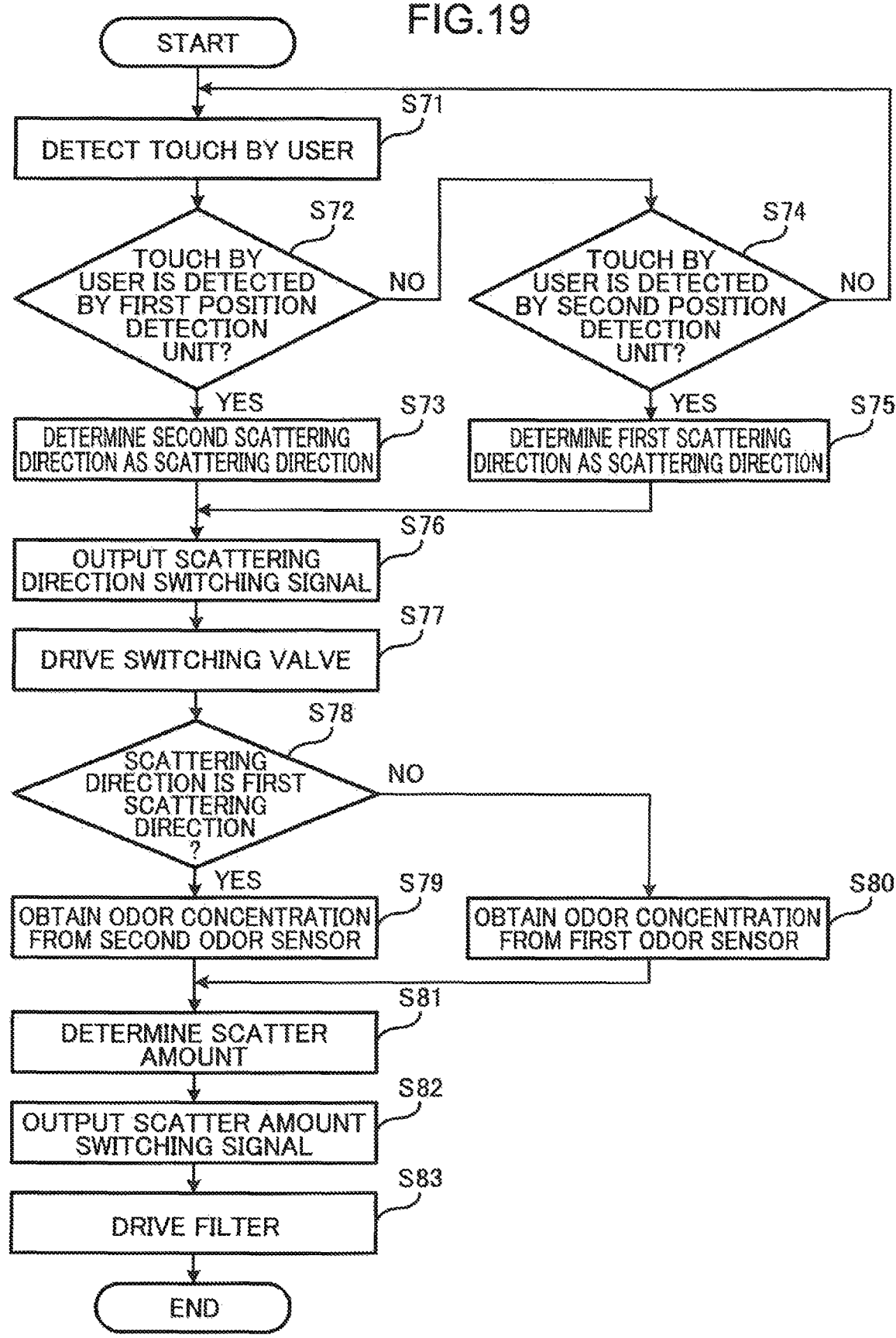
FIG. 19 is a flow chart for describing operation of the scattering device in the fifth embodiment of the present disclosure.

FIG. 19 is a flow chart for describing operation of the scattering device in the fifth embodiment of the present disclosure.

Since processing in Step S71 to S77 is the same as the processing in Step S1 to Step S7 shown in FIG. 6, description thereof will be omitted.

Next, in Step S78, the scatter amount determination unit 127 determines whether or not a scattering direction determined by the scattering direction determination unit 121 is the first scattering direction.

Here, when determination is made that the scattering direction is the first scattering direction (YES in Step S78), the scatter amount determination unit 127 obtains an odor concentration from the second odor sensor 182 in Step S79.

By contrast, when determination is made that the scattering direction is not the first scattering direction, i.e., when determination is made that the scattering direction is the second scattering direction (NO in Step S78), the scatter amount determination unit 127 obtains an odor concentration from the first odor sensor 181 in Step S80.

Next, in Step S81, the scatter amount determination unit 127 determines a scatter amount of an aromatic substance according to an odor concentration measured by the first odor sensor 181 or the second odor sensor 182. In a case where the odor concentration measured by the first odor sensor 181 or the second odor sensor 182 is higher than the first threshold value, the scatter amount determination unit 127 determines the scatter amount of an aromatic substance to be the largest first scatter amount. In a case where the odor concentration measured by the first odor sensor 181 or the second odor sensor 182 is equal to or higher than the second threshold value and equal to or smaller than the first threshold value, the scatter amount determination unit 127 determines the scatter amount of an aromatic substance to be the second largest second scatter amount. In a case where the odor concentration measured by the first odor sensor 181 or the second odor sensor 182 is smaller than the second threshold value, the scatter amount determination unit 127 determines the scatter amount of an aromatic substance to be the smallest third scatter amount.

Next, in Step S82, the scatter amount switching unit 128 outputs, to the filter driving unit 152, the scatter amount switching signal for switching a scatter amount of an aromatic substance to the scatter amount determined by the scatter amount determination unit 127. The scatter amount switching unit 128 outputs, to the filter driving unit 152, the scatter amount switching signal for switching a scatter amount of an aromatic substance to any of the first scatter amount, the second scatter amount, and the third scatter amount determined by the scatter amount determination unit 127.

Next, in Step S83, the filter driving unit 152 drives the filter 151 based on the scatter amount switching signal output from the scatter amount switching unit 128. The filter driving unit 152 causes the filter 151 to rotate such that, out of the first opening portion 1511, the second opening portion 1512, and the third opening portion 1513, an opening portion corresponding to the scatter amount determined by the scatter amount determination unit 127 moves to the front of the storage container 1361.

In a case where the user 106 moves from the first room 101 to the second room 102 in this manner, an odor concentration in the first room 101 is measured to determine a scatter amount of liquid, powder, or gas according to the measured odor concentration of the first room 101. Accordingly, when, for example, the odor concentration of the first room 101 is high, by increasing the amount of liquid, powder, or gas to be scattered in the second room 102, it is possible to allow the user 106 to more reliably recognize scent.

In the fifth embodiment, in a case where the user 106 moves from the first room 101 to the second room 102, the scatter amount determination unit 127 may obtain an odor concentration of the second room 102 measured by the second odor sensor 182 at a movement destination. Then, the scatter amount determination unit 127 may determine the amount of an aromatic substance to be scattered in the direction from the proximity of the doorway 104 toward the second room 102 such that the obtained odor concentration becomes a predetermined odor concentration.

Also in the fifth embodiment, in a case where the user 106 moves from the first room 101 to the second room 102, the scatter amount determination unit 127 may obtain the odor concentration of the second room 102 measured by the second odor sensor 182 at the movement destination. Then, in a case where the obtained odor concentration is equal to or higher than a threshold value, the scatter amount determination unit 127 may determine not to scatter an aromatic substance.

Also in the fifth embodiment, in a case where the user 106 moves from the first room 101 to the second room 102, the scatter amount determination unit 127 may obtain the odor concentration of the second room 102 measured by the second odor sensor 182 at the movement destination. Then, in a case where the obtained odor concentration is equal to or higher than a threshold value, the scatter amount determination unit 127 may determine to scatter an aromatic substance. Thereafter, the scatter amount determination unit 127 may determine a scatter amount of an aromatic substance based on the odor concentration in the first room 101 measured by the first odor sensor 181.

In each of the above embodiments, each component may be configured by dedicated hardware or realized by executing a software program suitable for each component. Each component may be realized also by reading and executing, by a program execution unit such as a CPU or a processor, a software program recorded in a recording medium such as a hard disk or a semiconductor memory.

A part or all of the functions of the devices according to the embodiments of the present disclosure are realized by an LSI (Large Scale Integration), which is typically an integrated circuit. The functions may be individually formed into one chip or may be formed partly or in its entirety into one chip. An integrated circuit may not exclusively be realized as an LSI but may be realized as a dedicated circuit or a general-purpose processor. It is also possible to use an FPGA (Field Programmable Gate Array) programmable after the production of an LSI, or to use a reconfigurable processor in which connection and setting of a circuit cell in an LSI is reconfigurable.

It is also possible to realize a part or all of the functions of the devices according to the embodiments of the present disclosure by executing a program by a processor such as a CPU or the like.

Numerals used in the foregoing are all exemplification for specifically describing the present disclosure and are not limited to those exemplified in the present disclosure.

The order of execution of the respective steps shown in the above flow charts is exemplification for specifically describing the present disclosure and can be the order other than that described above within a range in which the same effect can be obtained. A part of the above steps may be executed simultaneously (in parallel) with the other steps.

The technique according to the present disclosure is useful for a technique for scattering liquid, powder, or gas because liquid, powder, or gas can be scattered in a direction in which a user heads.

This application is based on Japanese Patent application No. 2019-112951 filed in Japan Patent Office on Jun. 18, 2019, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. A scattering device which scatters liquid, powder, or gas, the scattering device comprising:
a detection unit which detects a position of a user passing through a doorway formed between a first space and a second space adjacent to the first space;
a scattering direction determination unit which determines a scattering direction in which the liquid, the powder, or the gas is scattered from a proximity of the doorway based on the position of the user detected by the detection unit; and
a scattering unit arranged in the proximity of the doorway to scatter the liquid, the powder, or the gas toward the scattering direction determined by the scattering direction determination unit.

2. The scattering device according to claim 1, wherein the scattering direction determination unit determines a direction in which the user moves from the proximity of the doorway as the scattering direction.

3. The scattering device according to claim 1, wherein the liquid, the powder, or the gas includes an aromatic substance.

4. The scattering device according to claim 3, wherein the aromatic substance to be scattered when the user moves from the first space to the second space and the aromatic substance to be scattered when the user moves from the second space to the first space are different from each other.

5. The scattering device according to claim 1, wherein
the doorway includes a door, and
the scattering unit includes:
a first scattering opening provided in proximity to the door on a first space side to scatter the liquid, the powder, or the gas;
a second scattering opening provided in proximity to the door on a second space side to scatter the liquid, the powder, or the gas;
a duct connected to the first scattering opening and the second scattering opening;
a pump which sends air to the duct by using power of the user for opening the door;
a storage unit provided in the duct to store the liquid, the powder, or the gas and send out the liquid, the powder, or the gas as a result of passing of the air sent from the pump; and
a switching unit which switches a sending destination of the liquid, the powder, or the gas sent out from the storage unit to one of the first scattering opening and the second scattering opening.

6. The scattering device according to claim 1, further comprising:
a time obtaining unit which obtains current time; and
a kind determining unit which determines a kind of the liquid, the powder, or the gas according to the current time obtained by the time obtaining unit.

7. The scattering device according to claim 1, wherein
the doorway includes a door, the scattering device further comprising:
a load measuring unit which measures a load applied on the door when the user opens the door;
a user information storage unit which stores user information that correlates identification information for identifying the user, age of the user, gender of the user, and a kind of the liquid, the powder, or the gas;
an estimation unit which estimates age and gender corresponding to the load measured by the load measuring unit; and
a kind specifying unit which refers to the user information stored in the user information storage unit to specify a kind of the liquid, the powder, or the gas correlated with the age and the gender estimated by the estimation unit.

8. The scattering device according to claim 1, wherein
the doorway includes a door, the scattering device further comprising:
a load measuring unit which measures a load applied on the door when the user opens the door;
an acceleration measuring unit which measures an acceleration of the door when the user opens the door;
a prediction unit which inputs, to a prediction model obtained by machine learning using teaching data with the load and the acceleration as input data and emotion of the user as output data, the load measured by the load measuring unit and the acceleration measured by the acceleration measuring unit, and predicts, as emotion of the user when the user opens the door, emotion output from the prediction model; and
a kind determining unit which determines a kind of the liquid, the powder, or the gas according to the emotion predicted by the prediction unit.

9. The scattering device according to claim 1, wherein
when the user moves from the first space to the second space, the scattering direction determination unit determines, as the scattering direction, a direction from the proximity of the doorway toward the second space,
the scattering device further comprising:
an odor sensor which measures an odor concentration in the first space; and
a scatter amount determination unit which determines a scatter amount of the liquid, the powder, or the gas according to the odor concentration of the first space measured by the odor sensor when the user moves from the first space to the second space.

10. A door comprising the scattering device according to claim 1.

* * * * *